(12) United States Patent
Minko et al.

(10) Patent No.: US 8,124,051 B2
(45) Date of Patent: Feb. 28, 2012

(54) COMPLEX DRUG DELIVERY COMPOSITION AND METHOD FOR TREATING CANCER

(75) Inventors: Tamara Minko, Edison, NJ (US);
Patrick J. Sinko, Lebanon, NJ (US);
Stanley Stein, East Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 226 days.

(21) Appl. No.: 12/163,574

(22) Filed: Jun. 27, 2008

(65) Prior Publication Data

US 2008/0280813 A1    Nov. 13, 2008

Related U.S. Application Data

(63) Continuation of application No. 10/780,137, filed on Feb. 17, 2004, now abandoned.

(60) Provisional application No. 60/447,935, filed on Feb. 19, 2003, provisional application No. 60/463,135, filed on Apr. 14, 2003.

(51) Int. Cl.
*A61P 35/00* (2006.01)
*A61K 38/09* (2006.01)
*A61K 38/10* (2006.01)

(52) U.S. Cl. ............... 424/1.45; 514/19.3; 514/21.4; 514/21.6

(58) Field of Classification Search .................. None
See application file for complete search history.

(56) References Cited

U.S. PATENT DOCUMENTS

| | | | |
|---|---|---|---|
| 6,258,774 B1 | 7/2001 | Stein et al. | |
| 6,428,788 B1 | 8/2002 | Debinski et al. | |
| 6,548,062 B2 * | 4/2003 | Buchkovich et al. | 424/133.1 |

FOREIGN PATENT DOCUMENTS

| | | |
|---|---|---|
| WO | WO97/19954 | 6/1997 |
| WO | 0191789 | 12/2001 |
| WO | WO 0191798 A2 * | 12/2001 |

OTHER PUBLICATIONS

Chatzistamou et al. (Clinical Cancer Research 2000; 6: 4158-4165.*
Azar et al (Apoptosis, 2000, vol. 5, pp. 531-542).*
Nagy et al, Current Pharmaceutcial Design, 2005, vol. 11, pp. 1167-1180).*
Chatzistamou et al., "Effective Treatment of Metastatic MDA-MB-435 Human Estrogen Independent Breast Carcinomas With a Targeted Cytotoxic Analogue of Luteinizing Hormone-Releasing Hormone AN-2071", Clinical Cancer Research, 2000, pp. 4158-4165, vol. 6.
Conover et al., "Camptothecin Delivery Systems: The Antitumor Activity of a Camptothecin-20-0-Polyetheylene Glycol Ester Transport Form", Anticancer Res. 1997, pp. 3361-3368, vol. 17.
Dillman, "Monoclonal Antibodies for Treating Cancer", Annals of Internal Medicine, 1989, pp. 592-603, vol. 111.
Dipaola et al., "Targeting Apoptosis in Prostate Cancer", Hematol. Oncol. Clin. North Am. 2001, pp. 509-524, vol. 15.
Gura, "Systems for Identifying New Drugs Are Often Faulty", Science, 1997, pp. 1041-1042, vol. 278.
Jain, "Barriers to Drug Delivery in Solid Tumors", Scientific American, Jul. 1994, pp. 58-65, vol. 271(1).
Kopecek et al., "HPMA copolymer-anticancer drug conjugates: design, activity, and mechanism of action", Eur. J. Pharm. Biopharm 2000, pp. 61-81, vol. 50.
Kopecek et al., Water soluble polymers in tumor targeted delivery:, J. Controlled Rel. 2001, pp. 147-158, vol. 74.
Lu et al., "Design of novel bioconjugates for targeted drug delivery", J. Controlled Rel. Jan. 17, 2002, pp. 165-173, vol. 78.
Chandna, Pooja et al., "Multifunctional Tumor-Targeted Polymer-Peptide-Drug Delivery System for Treatment of Primary and Metastatic Cancers", Pharm Res, 2010, pp. 2296-2306, vol. 27.
Chandna, Pooja et al., "Targeted Proapoptotic Anticancer Drug Delivery System", Molecular Pharmaceutics, 2007, pp. 668-678, vol. 4, No. 5.
Dharap, Sonia S. et al., "Molecular Targeting of BCL2 and BCLXL Proteins by Synthetic BCL2 Homology 3 Domain Peptide Enhances the Efficacy of Chemotherapy", The Journal of Pharmacology and Experimental Therapeutics, 2006, pp. 992-998, vol. 316, No. 3.
Dharap, S. S. et al., "Tumor-specific targeting of an anticancer drug delivery systen by LHRH peptide", PNAS, 2005, pp. 12962-12967, vol. 102, No. 36.
Khandare, Jayant J. et al., "Novel Polymeric Prodrug with Multivalent Components for Cancer Therapy", The Journal of Pharmacology and Experimental Therapeutics, 2006, pp. 929-937, vol. 317, No. 3.
Saad, Maha et al., "Receptor targeted polymers, dendrimers, liposomes: Which nanocarrier is the most efficient for tumor-specific treatment and imaging?", Journal of Controlled Release, 2008, pp. 107-114, vol. 130.
Taratula, Oleh et al., "Surface-engineered targeted PPI dendrimer for efficient intracellular and intratumoral siRNA delivery", Journal of Controlled Release, 2009, pp. 284-293, vol. 140.
Michaelis et al., "Coupling of the antitumoral enzyme bovine seminal ribonuclease to polyethylene glycol chains increases its systemic efficacy in mice" Anitcancer Drugs, pp. 149-154, vol. 13, 2002.
Minko et al., "Advanced Drug Delivery Systems in Cancer Chemotherapy", Disease Management and Clinical Outcomes, 2001, pp. 48:54, vol. 3.
Minko et al., "Chronic exposure to HPMA copolymer-bound adriamycin does not induce multidrug resistance in a human ovarian carcinoma cell lines", J Controlled Rel. 1999, pp. 133-148, vol. 59.
Minko et al., "Comparison of the Anticancer Effect of Free and HPMA copolmer-Bound Adriamycin in Human Ovarian Carcinoma Cells", Pharm. Res. 1999, pp. 986-996, vol. 16(7).
Minko et al., "Efficacy of the Chemotherapeutic Action of HPMA Copolymer-Bound in Doxrubicin in a Solid Tumor Model of Ovarian Carcinoma", Int. J. Cancer 2000, pp. 108-117, vol. 86.

(Continued)

*Primary Examiner* — Karen Canella
(74) *Attorney, Agent, or Firm* — Fox Rothschild LLP

(57) ABSTRACT

The present invention relates to compositions and methods for producing a complex drug delivery system which specifically targets cancer cells, has an increase in cellular uptake, is cytotoxic, and suppresses antiapoptotic cellular defenses.

17 Claims, 3 Drawing Sheets

OTHER PUBLICATIONS

Minko et al., "Enhancing the anticancer efficacy of camptothecin using biotinylated poly (ethyleneglycol) conjugates in sensitive and multidrug-resistant human ovarian carcinoma cells", Cancer Chemother Pharmacol. 2002, pp. 143-150, vol. 50.

Minko et al., "HPMA copolymer bound adriamycin overcomes MDR1 gene encoded resistance in a human ovarian carcinoma cell line," J. Controlled Rel. 1998, pp. 223-233, vol. 54.

Minko et al., "Preliminary evaluation of caspases-dependent apoptosis signaling pathways of free and HPMA copolymer-bound doxorubicin in human ovarian carcinoma cells", J. Control. Rel. 2001, pp. 227-237, vol. 71.

Minko et al., "The Influence Cytotoxicity of Macromolecules and of VEGF Gene Modulated Vascular Permeability on the Enhanced Permeability and Retention Effect in Resistant Solid Tumors", Pharm. Res. 2000, pp. 505-514, vol. 17.

Pechar et al., "Poly(ethylene glycol) Multiblock Copolymer as a Crrier of Anti-Cancer Drug Doxorubicin", Bioconjugate Chemistry, 2000, pp. 131-139, vol. 11.

Weiner, "An Overview of Monoclonal Antibody Therapy of Cancer", Seminars Oncology, Nov. 4, 1999, pp. 41-50, vol. 26.

* cited by examiner

SEQUENCE LISTING

<160> NUMBER OF SEQ ID NOS: 4

<210> SEQ ID NO 1
<211> LENGTH: 19
<212> TYPE: PRT
<213> ORGANISM: Artificial Sequence
<220> FEATURE:
<223> OTHER INFORMATION: Synthetic BH3 domain peptide

<400> SEQUENCE: 1

Met Gly Gln Val Gly Arg Gln Leu Ala Ile Ile Gly Asp Asp Ile Asn
1               5                   10                  15

Arg Arg Tyr

<210> SEQ ID NO 2
<211> LENGTH: 16
<212> TYPE: PRT
<213> ORGANISM: Artificial Sequence
<220> FEATURE:
<223> OTHER INFORMATION: Antennapedia internalization peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: LHRH peptide analog

<400> SEQUENCE: 3

Gln His Trp Ser Tyr Lys Leu Arg Pro
1               5

```
<210> SEQ ID NO 4
<211> LENGTH: 20
<212> TYPE: PRT
<213> ORGANISM: Artificial Sequence
<220> FEATURE:
<223> OTHER INFORMATION: Synthetic BH3 peptide analog

<400> SEQUENCE: 4

Met Gly Gln Val Gly Arg Gln Leu Ala Ile Ile Gly Asp Asp Ile Asn
1               5                   10                  15

Arg Arg Tyr Cys
            20
```

COMPLEX DRUG DELIVERY COMPOSITION AND METHOD FOR TREATING CANCER

INTRODUCTION

This application is a Continuation of U.S. application Ser. No. 10/780,137 filed Feb. 17, 2004, which, in turn, claims priority benefit under 35 U.S.C. §119(e) of U.S. Provisional Patent Application Ser. No. 60/463,135, filed Apr. 14, 2003 and U.S. Provisional Patent Application Ser. No. 60/447,935 filed Feb. 19, 2003. The disclosures of all three applications are incorporated herein by reference.

BACKGROUND OF THE INVENTION

A central issue in cancer chemotherapy is the severe toxic side effects of anticancer agents on healthy tissues, which invariably imposes dose reduction, treatment delay or even discontinuance of therapy (Fennelly (1995) *Clin. Cancer Res.* 1:575-582; Hanjani, et al. (2002) *Gynecol. Oncol.* 85:278-284; Kobayashi, et al. (2002) *Chronobiol. Int.* 19:237-251; Ross and Small (2002) *J. Urol.* 167:1952-1956; Markman, et al. (2002) *J. Clin. Oncol.* 20:2365-2369; Sehouli, et al. (2002) *Gynecol. Oncol.* 85:321-326). Cytotoxicity for healthy organs can be significantly diminished by employing a drug delivery system which targets cancer cells (Alvarez, et al. (2002) *Expert. Opin. Biol. Ther.* 2:409-417; Dass and Su (2001) *Drug Deliv.* 8:191-213; Kopecek, et al. (2001) *J. Controlled Rel.* 74:147-158; Kunath, et al. (2000) *Eur. J. Pharm. Biopharm.* 49:11-15; Minko, et al. (2001) *Dis. Manag. Clin. Outcomes* 3:48-54; Vasey, et al. (2002) *J. Clin. Oncol.* 20:1562-1569). The usage of these drug delivery systems prevents, in most cases, the uptake of the drug by normal cells and enhances the influx and retention of the drug in cancer cells.

A second factor that limits the success of chemotherapeutic treatment of ovarian carcinoma is the development of multidrug resistance (Fennelly (1995) supra). The term multidrug resistance (MDR) is used to describe the resistance against a broad spectrum of anticancer drugs after the treatment with a single agent. A membrane glycoprotein, termed P-glycoprotein, has been shown to be responsible for cross-resistance to a broad range of structurally and functionally distinct cytotoxic agents. P-glycoprotein, encoded in humans by the MDR1 gene, functions as an energy-dependent membrane pump to remove cytotoxic agents from the resistant cells (Szakacs, et al. (1998) *Pathol. Oncol. Res.* 4:251-257). In addition to P-glycoprotein, other transporters contributing to MDR of cancer cells, such as the multidrug resistance associated protein (MRP), have been identified (van Veen and Konings (1998) *Biochem. Biophys. Acta* 1365:31-36). The overexpression of genes encoding these drug efflux pumps and an increase in their activity are the main causes of pump resistance in human ovarian carcinoma (Minko, et al. (2001) supra; Hamaguchi, et al. (1993) *Cancer Res.* 53:5225-5232; Minko, et al. (1998) *J. Controlled Rel.* 54:223-233; Minko, et al. (1999) *J. Controlled Rel.* 59:133-148; Pakunlu, et al. (2003) *Pharmaceut. Res.* 20:351-359).

Several methods, including the use of antisense oligonucleotides targeted against mRNA encoded by genes of drug efflux pumps, were developed over the last decades to overcome or suppress multidrug resistance (Alahary, et al. (1998) *JPET* 286:419-428; Motomura, et al. (1998) *Blood* 91:3163-3171; Corrias and Tonini (1992) *Anticancer Res.* 12:1431-1438). While these compounds lead to an increase in intracellular drug concentration, they do not overcome the adaptive activation of cell death defense, also known as non-pump resistance (Minko, et al. (2001) supra). It is known that the up-regulation of the cellular antiapoptotic system plays a role in this second line of defense and BCL-2 family proteins are key proteins in this system (Gross, et al. (1999) *Genes Dev.* 13:1899-1911; Reed (1999) *J. Clin. Oncol.* 17:2941-2953). Unlike the drug efflux pump proteins, overexpression of BCL-2 protein does not interfere with the entry and accumulation of drugs in tumor cells. Instead, BCL-2 protein prevents drug-induced damage from being efficiently translated into cell death by preventing cytochrome c release from mitochondria which triggers the caspase cascade of apoptosis execution.

The BCL-2 protein family consists of two kinds of proteins with counter-modulating functions; a group that suppress apoptosis, if overexpressed, and a group that has the ability to induce apoptosis (Reed (1999) supra; Abate-Shen and Shen (2000) *Genes Dev.* 14:2410-2434; Lowe and Lin (2000) *Carcinogenesis* 21:485-495). Although the precise role of these proteins in apoptosis induction and development of resistance during cancer therapy remains unclear, it was found that the expression ratio of antiapoptotic members of BCL-2 protein family to proapoptotic members determines survival or death following an apoptotic stimulus (Oltvai, et al. (1993) *Cell* 74:609-619) Several studies have correlated the expression of BCL-2 family members with a survival advantage in ovarian cancer but failed to find an association with overall response to chemotherapy (Baekelandt, et al. (1999) *Clin. Oncol.* 17:2061; Herod, et al. (1996) *Cancer Res.* 56:2178-2184; Schuyer, et al. (2001) *Br. J. Cancer* 85:1359-1367). In contrast, BCL-2 overexpression has been reported to be associated with a poor prognosis and resistance to chemotherapy (Kassim, et al. (1999) *Clin. Biochem.* 32:333-338; Mano, et al. (1999) *Eur. J. Cancer* 35:1214-1219). These differences may be explained by the fact that clinical studies focus on the separate analysis of the expression of pro- or anti-apoptotic members of the BCL-2 protein family. Concurrently, it was shown that it is the ratio between the expression of anti- and proapoptotic proteins that determines cell death by apoptosis after chemotherapy (Reed (1999) supra; Oltvai, et al. (1993) supra; Schuyer, et al. (2001) supra).

The BCL-2 family is characterized by specific regions of homology termed BCL-2 homology (BH1, BH2, BH3, BH4) domains. These domains are critical to the function of these proteins, including their impact on cell survival and their ability to interact with other family members and regulatory proteins (Abate-Shen and Shen (2000) supra; Johnson (1999) *Endocrinology* 140:5465-5467). It was found that the BH3 domain of proapoptotic proteins from the BCL-2 family is responsible for the induction of apoptosis (Abate-Shen and Shen (2000) supra; Johnson (1999) *Endocrinology* 140:5465-5467; Cosulich, et al. (1997) *Curr. Biol.* 7:913-920). Furthermore, expression of small, truncated derivatives of the BAK protein containing the BH3 domain are sufficient for cell killing activity (Lutz (2000) *Biochem. Sci. Trans.* 28:51-56). Moreover, it was found that short synthetic peptides, corresponding to the minimal sequence of BH3 domain when bound to the antiapoptotic BCL-2 family proteins, suppress the cellular antiapoptotic defense (Minko, et al. (2001) supra; Lutz (2000) supra; Holinger, et al. (1999) *J. Biol. Chem.* 274:13298-13304; Minko, et al. (2002) *Cancer Chemother. Pharmacol.* 50:143-150). While, BH3 peptide may potentially improve traditional therapy of ovarian cancer by decreasing the resistance of cancer cells to chemotherapeutic agents, the practical use of the BH3 peptide is limited by its low permeation into cancer cells.

A targeted approach for producing a net increase in apoptosis induction during treatment of cancer to significantly increase cancer cell death and efficacy of chemotherapy is needed. The present invention meets this long-felt need.

SUMMARY OF THE INVENTION

One aspect of the present invention is a complex drug delivery composition for treating cancer. The composition includes at least two of the following components: a suppressor of antiapoptotic cellular defense, an anticancer agent, a cell-surface targeting moiety or a multifunctional carrier. In one embodiment, the components of the complex drug delivery composition are operably-linked. In another embodiment of the invention, the multifunctional carrier and cell-surface targeting moiety are the same molecule.

Another aspect of the present invention is a method of treating cancer using a complex drug delivery system which specifically targets cancer cells, has improved uptake, is cytotoxic, and suppresses antiapoptotic cellular defenses.

A further aspect of the invention is a method of producing a complex drug delivery composition. The method involves combining with a scaffold, at least two of the following components: a suppressor of antiapoptotic cellular defense, an anticancer agent, a cell-surface targeting moiety or a multifunctional carrier. In a particular embodiment, the complex drug delivery composition contains at least one molecule of a component combined with the scaffold.

DETAILED DESCRIPTION OF THE INVENTION

Figure 1:
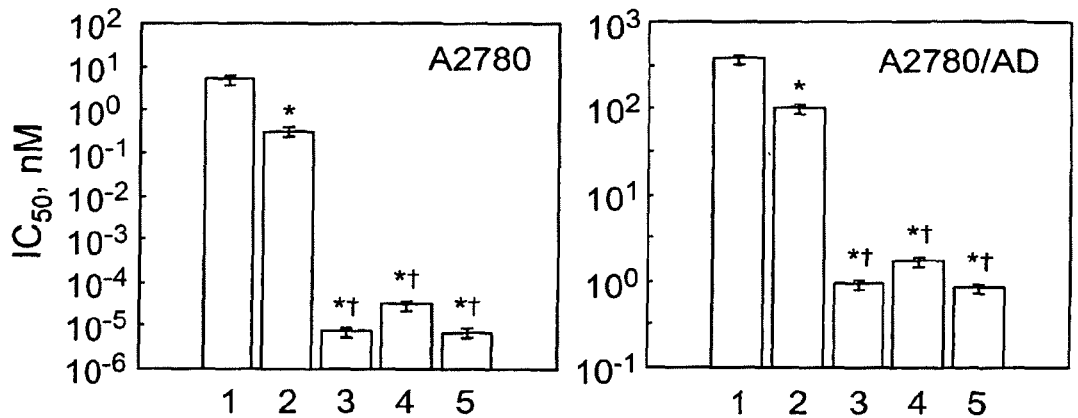
FIG. 1 demonstrates the Cytotoxicity of (1) CPT, (2) CPT-PEG, (3) CPT-PEG-BH3, (4) CPT-PEG-LHRH, and (5) a mixture of CPT-PEG-BH3 with CPT-PEG-LHRH in A2780 sensitive and A2780/AD multidrug resistant human ovarian carcinoma cells. Mean ±SD is shown. *P<0.05 compared with CPT. †P<0.05 compared with CPT-PEG.

Chemotherapeutic agents are known to induce programmed cell death or apoptosis. The activation of cellular antiapoptotic defenses that prevent the translation of drug-induced damage into cell death is a key factor in cellular, non-pump resistance to a broad spectrum of anticancer drugs. Thus, a net increase in apoptosis induction during cancer treatment could significantly increase cancer cell death and the efficacy of chemotherapy. Moreover, targeting an anticancer agent specifically to cancer cells has numerous benefits including the maintenance of a low blood-to-cell concentration ratio in order to reduce therapy-limiting side effects and increase anticancer effectiveness.

It has been shown that prolonged exposure or high concentrations of anticancer drugs leads to the development of drug resistance (Minko, et al. (2001) *Dis. Manag. Clin. Outcomes* 3:48-54; Minko, et al. (1999) *J. Controlled Rel.* 59:133-148; Pakunlu (2003) *Pharm. Res.* 20:351-359; Minko, et al. (1999) *Pharm. Res.* 16:986-996; Minko, et al. (2001) *J. Control. Rel.* 71:227-237). To analyze antiapoptotic resistance, the degree of apoptosis to doxorubicin (DOX), a traditional, well-established anticancer drug, was determined. The enrichment of cell lysate and media by mono- and oligonucleosomes was measured using a cell death detection ELISA kit. The expression of genes was measured by reverse transcription PCR (RT-PCR) using $\beta_2$-microglobulin ($\beta_2$-m) as an internal standard. The data showed that with low DOX concentrations, cells responded to the treatment by apoptosis. In contrast, cells that survived exposure to high DOX concentrations overexpressed the BCL-2 gene and developed resistance to apoptosis. Similar results were obtained after repeated incubation of human ovarian carcinoma cells with low doses of DOX (Minko, et al. (1999) supra; Minko, et al. (1999) supra) and after treatment of mice xenografts of ovarian carcinoma cells with DOX. It was found that DOX successfully induced apoptosis in tumor tissue and decreased the tumor size up to 25 days of treatment. Starting from the 25$^{th}$ day, overexpression of the BCL-2 gene and other antiapoptotic members of BCL-2 family was observed in tumor tissue; apoptosis induction attenuated and tumors started to grow progressively. Further, sensitive and multidrug resistance ovarian, breast, prostate, leukemia and lung cancer cell lines and tumor xenografts exhibited similar results and showed that several anticancer drugs simultaneously induced cell death and activated antiapoptotic defense by overexpression of antiapoptotic members of the BCL-2 protein family. Thus, suppression of this antiapoptotic cellular defense mechanism is desirable.

It has now been found that two or more of the components of a complex drug delivery composition provide an increase in the efficacy of cancer chemotherapy. Accordingly, the present invention provides compositions and methods for treating cancer using a complex drug delivery composition. The composition contains at least two, three, or four of the following components: a multifunctional carrier, a cell-surface targeting moiety, an anticancer agent, or a suppressor of antiapoptotic cellular defense.

While specific molecules are provided herein, these molecules are illustrative examples of the inventive composition and should not be construed as limitations thereof. It is contemplated that various combinations of each component can be tailored to include specific anticancer agents or cell-surface targeting moieties known to have activity or receptors, respectively, in specific cancers. The complex drug delivery composition of the invention is useful in treating cancers including, but not limited to, skin cancer, ovarian cancer, breast cancer, cervical cancer, colorectal cancer, prostate cancer, liver cancer, lung cancer, stomach cancer, bone cancer, and pancreatic cancer. In particular embodiments of the invention, the cancer is of a reproductive tissue, for example, ovarian cancer, breast cancer, cervical cancer, and prostate cancer.

One embodiment of the present invention is a suppressor of antiapoptotic cellular defense component of a complex drug delivery composition. A suppressor of antiapoptotic cellular defense specifically targets intracellular pathways responsible for resistance of cancer cells to chemotherapeutic agents thereby enhancing the activity of an anticancer agent. Exemplary antiapoptotic cellular defense components include BH3 peptides derived from BCL-2, Bax, or Bad (Shangary and Johnson (2002) *Biochemistry* 41(30):9485-95); BCL-2 antisense oligonucleotide (e.g., GENASENSE™) for blocking the production of the BCL-2 protein (Chanan-Khan (2003) *Eur. J. Haematol.* 70(4):269); at least an active portion of a Btf protein (Kasof, et al. (1999) *Mol. Cell. Biol.* 19(6):4390-404); or an antibody, or fragment thereof, which binds to Serine-70 or the antiproliferative domain (AP) of BCL-2 resulting in the inhibition of BCL-2/Bax binding.

By way of example, the effectiveness of a BH3 peptide (Met-Gly-Gln-Val-Gly-Arg-Gln-Leu-Ala-Ile-Ile-Gly-Asp-Asp-Ile-Asn-Arg-Arg-Tyr; SEQ ID NO:1) to increase cell death by inducing the mitochondrial dysfunction leading to necrosis was measured. BH3 peptide was delivered into human ovarian carcinoma cells by the Antennapedia (Ant) internalization sequence (Arg-Gln-Ile-lys-Ile-Trp-Phe-Gln-Asn-Arg-Arg-Met-Lys-Trp-Lys-Lys; SEQ ID NO:2). Mitochondrial function was assessed by flow cytometry analysis using the lipophilic cationic fluorescent probe 5,5',6,6'-tetrachloro-1,1',3,3'-tetraethylbenzimidazolcarbo-cyanine iodide (JC-1). This probe exists as a monomer, and upon excitation at 490 nm, emits light at 527 nm resulting in green fluorescence. At high mitochondrial transmembrane potential, JC-1 forms multimers, known as J-aggregates, and emits light at 590 nm upon excitation at 490 nm resulting in red fluorescence. Therefore, the red/green fluorescence ratio measured by flow cytometry reflects the number of functioning mitochondria. Ant alone was not toxic up to the highest possible concentration (1 mg/mL). In contrast, the combination of Ant with BH3 peptide led to a significant increase in toxicity of the peptide. The measured $IC_{50}$ dose of Ant-BH3 peptide was 51±9.8 nM, which is several times lower than the $IC_{50}$ of DOX (484±36.4 nM, P<0.05). The effect of the Ant-BH3 peptide on mitochondrial transmembrane potential was also determined. The results of these studies demonstrated that Ant-BH3 peptide did not lead to statistically significant changes in mitochondrial membrane potential.

The influence of BH3 peptide, delivered by an Ant-BH3 fusion peptide, on the expression of proteins and genes encoding proapoptotic and antiapoptotic members of the BCL-2 protein family was determined. The expression of genes was measured by RT-PCR using $\beta_2$-m as an internal standard. Cells were incubated 48 hours with an $IC_{50}$ dose of Ant-BH3 peptide. The results of these studies showed that BH3 peptide did not significantly change the expression of BAD, BAX, BCL-G, BID, BIM, BNIP-1, HRK and NIX genes and up-regulated the expression of BCL-XS, BIK, BNIP-2 and MSL-1S genes encoding proapoptotic members of the BCL-2 protein family (Table 1). In contrast, another proapoptotic gene, BNIP-3, was down-regulated after exposure to BH3 peptide. Thus, most of the examined proapoptotic members of the BCL-1 family were unchanged or up-regulated.

TABLE 1

| Gene | Expression, % of Control |
|---|---|
| BAD | 90 ± 8 |
| BAX | 91 ± 9 |
| BCL-G | 87 ± 11 |
| BCL-XS | 168 ± 11* |
| BID | 99 ± 9 |
| BIK | 511 ± 42* |
| BIM | 114 ± 17 |
| BNIP-1 | 93 ± 8 |
| BNIP-2 | 173 ± 14* |
| BNIP-3 | 69 ± 6* |
| HRK | 88 ± 10 |
| MLS-1S | 130 ± 11* |
| NIX | 89 ± 10 |

Means ± SD.
*P < 0.05 compared to control.

Further analysis showed that the BH3 peptide down-regulated the expression of AVEN, BAG, BCL-2, BCL-XL, and BFL genes encoding antiapoptotic members of the BCL-2 protein family. Simultaneously, the expression of three other antiapoptotic genes, DAD-1, MCL-1L and BCL-W did not significantly change after exposure to the BH3 peptide (Table 2). Thus, most of the genes encoding antiapoptotic members of the BCL-2 protein family were down-regulated by the BH3 peptide. In contrast, a peptide containing scrambled BH3 sequence did not change the expression of the genes examined.

TABLE 2

| Gene | Expression, % of Control |
|---|---|
| AVEN | 78 ± 2* |
| BAG | 56 ± 5* |
| BCL-2 | 66 ± 7* |
| BCL-XL | 64 ± 3* |
| BFL | 70 ± 2* |
| DAD-1 | 99 ± 5 |
| MCL-1L | 108 ± 8 |
| BCL-W | 97 ± 8 |

Means ± SD.
*P < 0.05 compared to control.

These results indicated that BH3 peptide suppresses cellular antiapoptotic defense and activates, at a much lesser extent, a proapoptotic signal. Thus, the BH3 peptide shifts the ratio of proapoptotic:antiapoptotic members of the BCL-2 protein family toward the predominant expression of proapoptotic members, therefore inhibiting cellular antiapoptotic defense and increasing the ability of an anticancer agent to activate apoptosis. Accordingly, in one embodiment, a suppressor of antiapoptotic cellular defense of the targeted proapoptotic anticancer drug delivery composition of the invention is a BH3 peptide.

Another embodiment of the present invention is a cell-surface targeting moiety of a complex drug delivery composition. A cell-surface targeting moiety is defined as an agent which specifically targets the complex drug delivery composition to a cancer cell, in particular the cell-surface, and facilitates uptake into the cell. Exemplary targeting moieties include peptide hormones such as bombesin, stomatostatin and luteinizing hormone-releasing hormone (LHRH) or analogs thereof. Cell-surface receptors for peptide hormones have been shown to be overexpressed in tumor cells (Schally (1994) *Anti-Cancer Drugs* 5:115-130; Lamharzi, et al. (1998) *Int. J. Oncol.* 12:671-675) and the ligands to these receptors are known tumor cell targeting agents (Grundker, et al. (2002) *Am. J. Obstet. Gynecol.* 187(3):528-37; WO 97/19954). Carbohydrates such as dextran having branched galactose units (Ohya, et al. (2001) *Biomacromolecules* 2(3):927-35), lectins (Woodley (2000) *J. Drug Target.* 7(5):325-33), and neoglycoconjugates such as Fucalphal-2Gal (Galanina, et al. (1998) *Int. J. Cancer* 76(1):136-40) can also be used as targeting moieties to treat, for example, colon cancer. It is further contemplated that an antibody or antibody fragment which binds to a protein or receptor, which is specific to a tumor cell, can be used to as a cell-surface targeting moiety. In particular embodiments, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. Exemplary antibody targeting moieties include bispecific monoclonal antibodies composed of an anti-histamine-succinyl-glycine Fab' covalently coupled with an Fab' of either an anticarcinoembryonic antigen or an anticolon-specific antigen-p antibody (Sharkey, et al. (2003) *Cancer Res.* 63(2):354-63).

By way of illustration, RT-PCR analysis was conducted to determine the expression of the LHRH receptor in cancer cells. Total cellular. RNA was isolated from cancer cells and from different healthy human tissues (Multiple Tissue cDNA Panels; Clontech, Palo Alto, Calif.). $\beta_2$-m was used as an internal standard and also to confirm the efficacy of the PCR. These studies showed that the LHRH receptor (LHRHR) gene is overexpressed in human ovarian, breast and prostate cancer cells and not expressed in LHRHR-negative SKOV-3 cells. The expression of the LHRHR gene in healthy human tissues, such as the lung, liver, kidney, spleen, muscle, heart and thymus, was below the detection limits of PCR, while the $\beta_2$-m gene was expressed in all tissues. Moreover, LHRH receptor was overexpressed in pituitary gland.

To compare the expression of the LHRHR in healthy human reproductive tissues and corresponding cancers, PCR analysis was conducted on cDNA generated from RNA isolated from healthy and cancerous reproductive tissues from the same subject. Tissues analyzed were human ovary, uterus, cervix, and breast tissues. The results of this analysis demonstrated that the expression of LHRHR in cancer is significantly (4-6 times) higher than in corresponding healthy tissue taken from the same subjects. These data indicate that using a ligand to LHRHR (e.g., LHRH peptide), as a cell-surface targeting moiety for targeting an anticancer agent specifically to LHRHR-positive cancer tissues, can effectively prevent adverse side effects on LHRHR-negative non-reproductive tissues and significantly minimize these effects on healthy reproductive tissues.

An active analog of the LHRH peptide, LHRH-Lys$^6$-des-Gly$^{10}$-Pro$^9$-ethylamide (Gln-His-Trp-Ser-Tyr-DLys-Leu-Arg-Pro-NH-Et (SEQ ID NO:3), was used to target the BH3 peptide to ovarian cancer cells. The cytotoxicity of BH3, LHRH and LHRH-BH3 peptides was assessed by the modified MTT assay (Minko, et al. (1998) *J. Controlled Rel.* 54:223-233). LHRHR-positive A2780 human cancer cells were incubated separately with 45 different concentrations of peptides. The results indicated that the BH3 peptide alone was not toxic up to the maximal possible concentration limited by its solubility (1 mg/mL). This reflects a low capacity of BH3 to penetrate cancer cells. Further analysis showed that LHRH peptide alone also did not have any significant toxicity up to the highest possible concentration. Similar results were obtained on other cancer cells that do and do not express LHRHR. In contrast, LHRH-BH3 peptide was toxic in human ovarian cancer cells having a mean value of drug concentration which inhibits growth by 50% relative to non-treated control cells (IC$_{50}$) of 3.97±0.33 ng/mL. These data indicate that LHRH significantly enhances cellular uptake of BH3 peptide in LHRHR-positive cancer cells. In contrast, LHRH-BH3 peptide was not toxic in cancer cells not expressing LHRHR. Further, non-targeted Ant-BH3 peptide was toxic in both LHRHR-positive and negative cancer cells. It was also found that BH3 peptide conjugates with scrambled LHRH peptide sequences did not exhibit toxicity up to the maximum possible concentration. Thus, the LHRH peptide specifically targets cancer cells expressing the LHRHR and facilitates the uptake of LHRH-conjugates.

To analyze the dependence of the cytotoxicity of LHRH-BH3 peptide on the expression of the targeted LHRH receptor gene, the IC$_{50}$ doses of the LHRH-BH3 peptide and the expression of the LHRHR gene in human A2780 ovarian, MCF-7 breast and PC-3 prostate cancer cells were determined. LHRHR expression was 1.6-fold and 3.2-fold less in MCF-7 and PC-3 cells, respectively, than LHRHR expression in A2780 cells. Correspondingly, the toxicity of LHRH-BH3 peptide in MCF-7 and PC-3 cells was more than 10- and 100-fold, respectively, less then LHRH-BH3 peptide toxicity in A2780 ovarian carcinoma cells. Further analysis revealed a strong exponential correlation between the IC$_{50}$ dose of LHRH-BH3 peptide and the expression of LHRHR gene in cancer cells with a coefficient correlation of r$^2$>0.99.

The extent to which the cytotoxicity of LHRH-BH3 peptide was associated with LHRHR binding was determined by competitive binding assays. A2780 human ovarian carcinoma cells were incubated with 45 different concentrations of LHRH peptide in the presence of LHRH-BH3 peptide and cell viability was measured. Competitive binding of LHRH peptide to LHRHR limited cytotoxicity of the LHRH-BH3 conjugate in a concentration-dependent manner. Logarithmic regression analysis indicated that at a concentration of 7.3× 10$^{-5}$ ng/mL LHRH decreased cytotoxicity of LHRH-BH3 peptide by 50%; a very low EC$_{50}$ dose of LHRH peptide.

The effect of the LHRH-BH3 peptide on apoptosis was analyzed by measuring transcriptional and translational levels and activity of human caspases. RT-PCR analysis indicated that caspases 1, 4, and 5 were not expressed in untreated A2780 human ovarian carcinoma cells as well as cells treated with BH3 peptide. Incubation of these cells with Ant-BH3 and LHRH-BH3 resulted in an up-regulation of APAF-1 and SMAC (Second Mitochondrial-Derived Activator of Caspase) (Table 3). This increase in expression results in the conversion of inactive procaspase 9 into active caspase 9. Active caspase 9, in turn, activates a cascade of downstream caspases, as evidenced by increased expression levels, which subsequently leads to induction of apoptosis.

TABLE 3

| | Mean Gene Expression ± SD | |
| --- | --- | --- |
| Gene Name | Untreated Control Cells | Ant-BH3 Treated Cells |
| APAF-1 | 24 ± 2 | 78 ± 3* |
| SMAC | 40 ± 3 | 77 ± 2* |
| Caspase 2 | 98 ± 7 | 134 ± 5* |
| Caspase 3 | 10 ± 1 | 60 ± 5* |
| Caspase 6 | 37 ± 1 | 77 ± 5* |
| Caspase 7 | 84 ± 6 | 88 ± 8 |
| Caspase 8 | 68 ± 6 | 70 ± 6 |

TABLE 3-continued

| | Mean Gene Expression ± SD | |
|---|---|---|
| Gene Name | Untreated Control Cells | Ant-BH3 Treated Cells |
| Caspase 9 | 60 ± 5 | 126 ± 11* |
| Caspase 10 | 33 ± 2 | 48 ± 3* |

Cells were incubated 48 hours with $IC_{50}$ dose of peptide. Gene expression was calculated as the ratio of band intensity of gel-separated RT-PCR products of the gene of interest to that of the $\beta_2$-m internal standard.
*P < 0.05 compared with untreated control cells.

Further, direct measurements of caspase 3 and 9 activity using a colorimetric protease assay (Pakunlu, et al. (2003) supra; Minko, et al. (2002) *Cancer Chemother. Pharmacol.* 50:143-150) indicated that LHRH-peptide activated both caspases.

Induction of apoptosis in human ovarian carcinoma cells was further analyzed by measuring the enrichment of cell cytoplasmic fraction (lysate) and media by mono- and oligo-nucleosomes using a cell detection ELISA (Minko, et al. (2002) supra; Minko, et al. (1999) *Pharm. Res.* 16:986-996) and by detecting the presence of single- and double-stranded DNA breaks or nicks occurring at early stages of apoptosis. In situ detection of DNA breaks or nicks was carried out using a terminal deoxynucleotidyl transferase-mediated dUTP-fluorescein nick end-labeling method (TUNEL). Apoptotic cells were fixed and permeabilized using well-established methods (Pakunlu, et al. (2003) supra; Minko, et al. (2002) supra; Minko, et al. (1999) supra). Subsequently, the cells were incubated with the TUNEL reaction mixture. The label was then incorporated at the damaged sites of DNA and visualized by fluorescence microscopy and quantified by flow cytometry. The results of these studies indicated that incubation of A2780 human ovarian carcinoma cells with 4 ng/mL of LHRH-BH3 peptide induced apoptosis.

These results indicate that LHRH peptide provides targeting to the LHRHR receptor and that a complex drug delivery composition using LHRH peptide as a cell-surface targeting moiety is highly toxic to tumors which overexpress LHRHR and several orders of magnitude less toxic to normal tissues having undetectable levels of LHRHR expression. Accordingly, in one embodiment of the present invention, a cell-surface targeting moiety of a complex drug delivery composition is LHRH.

Another embodiment of the present invention is a multifunctional carrier component of a complex drug delivery composition. A multifunctional carrier component is typically a polymer having at least two of the following characteristics: providing multiple sites (e.g., amino or thiol groups) for attachment of other components; functioning as a spacer so that other components of the complex drug delivery composition act independently, thereby avoiding possible steric hinderance; extending the half-life of the active components; and functioning to increase the molecular weight of the complex drug delivery composition to an optimal molecular weight for enhanced targeting. Exemplary natural and synthetic multifunctional carriers include, but are not limited to, N-(2-hydroxypropyl)methacrylamide (HPMA) copolymer, styrene-maleinanhydride copolymer, polyethylene glycol (PEG), polypropylene oxide, polyglutamic acid, dextran as well as liposomes or nanoparticles. In particular embodiments of the present invention, PEG is used as a multifunctional carrier. PEG provides an extended half-life; the half-life of small drugs conjugated with PEG can increase from minutes to hours (Conover, et al. (1997) *Anticancer Res.* 17:3361-3368). The large size of PEG slows down elimination through the kidneys, while the bulky, chemically-inert PEG chains protect active components from enzymatic degradation and other destructive factors during transport in the blood stream. When using PEG in the composition of the present invention, the molecular weight can range from 200-35000, or 200-8000, or 200-3500 and can be dependent on the total molecular weight of the other components of the complex drug delivery composition so that an optimal molecular weight of said composition is achieved.

A further embodiment of the present invention is an anticancer agent component of a complex drug delivery composition. Chemotherapy and therapeutic anticancer agents which can be used in the complex drug delivery composition of the invention include, cytotoxic agents such as Taxol, Cytochalasin B, Gramicidin D, Ethidium Bromide, Emetine, Mitomycin, Etoposide, Tenoposide, Vincristine, Vinblastine, camptothecin (CPT), Colchicin, Doxorubicin, Daunorubicin, Mitoxantrone, Mithramycin, Actinomycin D, 1-Dehydrotestosterone, Glucocorticoids, Procaine, Tetracaine, Lidocaine, Propranolol, and Puromycin and analogs or homologs thereof. Therapeutic agents include, but are not limited to, antimetabolites (e.g., Methotrexate, 6-Mercaptopurine, 6-Thioguanine, Cytarabine, 5-Fluorouracil, Decarbazine), alkylating agents (e.g., Mechlorethamine, Thiotepa, Chlorambucil, Melphalan, Carmustine (BCNU), Lomustine (CCNU), Cyclophosphamide, Busulfan, Dibromomannitol, Streptozotocin, Mitomycin C, Cis-Dichlorodiamine Platinum (II) (DDP), Cisplatin), anthracyclines (e.g., Daunorubicin (formerly Daunomycin) and Doxorubicin), antibiotics (e.g., Dactinomycin (formerly Actinomycin), Bleomycin, Mithramycin, and Anthramycin (AMC)), anti-mitotic agents (e.g., Vincristine and Vinblastine) and selective apoptotic agents such as APTOSYN® (Exisulind), PANZEM™ (2-methoxyestradiol), and VELCADE® (bortezomib) a proteasome inhibitor.

Anticancer agents for the treatment of ovarian cancer can include one or more of the following: Etoposide, Melphalan, Cisplatin, Carboplatin, CPT, Paclitaxel, Anthracyclines (e.g., Doxorubicin), Hexamethylamine (Altretamine), Progestins (e.g., Medroxyprogesterone acetate, Megestrole acetate), 5-Fluorouracil plus Leucovorin (to counteract folic acid antagonists), Ifosfamide, or Topotecan.

Anticancer agents for the treatment of breast cancer can include Doxorubicin, PANZEM™ (2-methoxyestradiol), Paclitaxel, Methotrexate, 5-Fluorouracil, Docetaxel, Thiotepa, Cisplatin, Estrogen receptor modulators such as Tamoxifen and Toremifene, Estrogens (e.g., diethylstilbestrol), Androgens (e.g., fluoxymesterone), Gonadotropin-Releasing Hormone (GnRH), Anastrozole, Aromatase inhibitors (antineoplastics), Vinorelbine tartrate, Gemcitabine hydrochloride, Progestins (e.g., Medroxyprogesterone acetate, Megestrole acetate), Trastuzumab (HERCEPTIN®), and Cyclophosphamide.

Anticancer agents for colorectal cancer treatment can include Oxaliplatin, 5-Fluorouracil, or Leucovorin.

Exemplary anticancer agents for the treatment of prostate cancer can include anti-androgens (e.g., Flutamide, Nilutamide, Bicalutamide, Cyproterone, Megestrol) and the Leuteinizing Hormone-Releasing Hormone analogues (e.g., Buserelin, Goserelin, Leuprolide).

Anticancer agents for liver cancer treatment can include 5-Fluorouracil, Leucovorin, Raltitrexed, Mitomycin C, and CPT-1.

Anticancer agents for the treatment of lung cancer can include Paclitaxel, Carboplatin, Vinorelbine tartrate, Gemcitabine hydrochloride, Etoposide, Doxorubicin, Ifosfamide, Docetaxel, Cyclophosphamide, Methotrexate, Lomustine (CCNU), Topotecan hydrochloride, and Cisplatin.

By way of example, CPT-conjugates were synthesized to analyze the efficacy of a multi-component, complex drug delivery composition. It has been shown that the conjugation of CPT to PEG-based polymer resulted in a 12-fold increase in the toxicity of CPT in both sensitive and multidrug resistant human ovarian carcinoma cancer cells (Minko, et al. (2002) supra). This effect may have resulted from the increased solubility, enhanced stability of the lactone form, increased cell uptake, and reduced efflux from target cells.

Cytotoxicity of CPT, CPT-PEG, CPT-PEG-BH3, and CPT-PEG-LHRH conjugates and the combination of CPT-PEG-BH3 with CPT-PEG-LHRH conjugates was analyzed using a modified MTT assay (Minko, et al. (1998) supra) in sensitive A2780 and multidrug resistant A2780/AD human ovarian carcinoma cells. CPT-PEG-BH3 and CPT-PEG-LHRH conjugates, as well as a combination thereof, dramatically decreased $IC_{50}$ doses (i.e., increased the toxicity) in both sensitive A2780 and resistant A2780/AD human ovarian carcinoma cells (FIG. 1).

The expression of genes encoding antiapoptotic members of the BCL-2 protein family (BCL-2 and BCL-XL), caspase activators (SMAC and APAF-1), caspase 9 (apoptosis inhibitor) and caspase 3 (apoptosis executor) as well as the activity of the caspases was measured after a 48-hour incubation of A2780 human ovarian carcinoma cells with CPT, CPT-PEG, CPT-PEG-BH3, or CPT-PEG-LHRH conjugates. Free CPT and the CPT-PEG conjugate activated both caspase-dependent pathways of apoptosis and cellular antiapoptotic defense. In contrast, the CPT-PEG-BH3 conjugate downregulated BCL-2 and BCL-XL genes, which in turn led to a more pronounced activation of caspase activators and caspases themselves.

Figure 2:
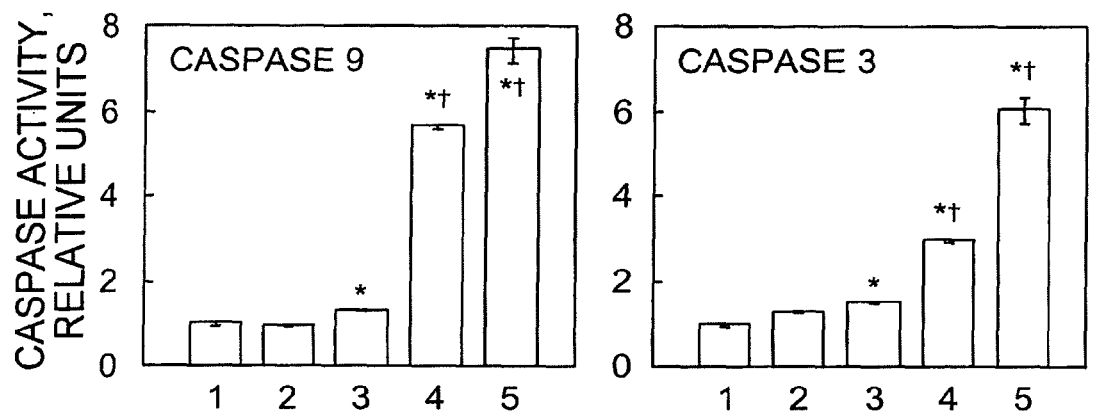
FIG. 2 demonstrates the activity of caspases 3 and 9 in A2780 human ovarian carcinoma cells exposed to a (1) control, (2) CPT, (3) CPT-PEG, (4) CPT-PEG-BH3, and (5) CPT-PEG-LHRH. Mean ±SD is shown. *P<0.05 compared with control. †P<0.05 compared with CPT.

Incorporation of the LHRH peptide into the CPT-PEG conjugate significantly increased the initiation of the caspase-dependent apoptosis pathway. Analysis of gene expression demonstrated that CPT-PEG-LHRH, as well as free CPT and CPT-PEG conjugate, induced both caspase-dependent signaling pathway of apoptosis and cellular antiapoptotic defense: activation of SMAC, APAF-1, caspases 9 and 3, BCL- and BCL-XL. However, the degree of activity of caspases induced by CPT-PEG-BH3 and CPT-PEG-LHRH was significantly higher when compared with free CPT and CPT-PEG conjugates (FIG. 2).

Figure 3:
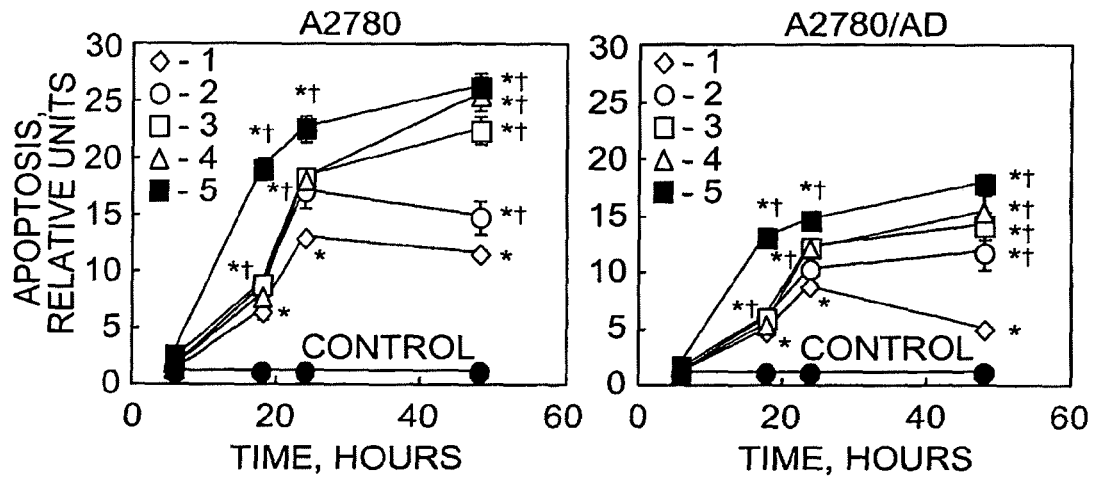
FIG. 3 demonstrates the time-dependent induction of apoptosis by (1) CPT, (2) CPT-PEG, (3) CPT-PEG-BH3, (4) CPT-PEG-LHRH conjugates, and (5) the combination of CPT-PEG-BH3 with CPT-PEG-LHRH in sensitive A2780 and multidrug resistance A2780/AD human ovarian carcinoma cells. Cells were incubated with CPT concentrations equivalent to $IC_{50}$ dose. The enrichment of control cells by histone-associated DNA fragments (mono- and oligonucleosomes) was set to 1 unit and the degree of apoptosis was expressed in the relative (to control) units. Mean ±SD are shown. *P<0.05 compared with control. †P<0.05 compared with CPT.

Targeting of CPT-PEG conjugates to the cell-surface and intracellular antiapoptotic cellular defense pathways was examined by incubating A2780 and multidrug resistant A2780/AD human ovarian carcinoma cells with free CPT, CPT-PEG, CPT-PEG-BH3 or CPT-PEG-LHRH conjugates, or the combination of CPT-PEG-BH3 with CPT-PEG-LHRH. The concentration of CPT (free and conjugated) in all experiments was 3 nM. Apoptosis was assessed by measuring the enrichment of cell cytoplasm by histone-associated DNA fragments (mono- and oligonucleosomes) and detecting the presence of single- and double-stranded DNA breaks or nicks using the TUNEL method. The former measurement detected time-dependent induction, while the latter measurement detected apoptosis after a 48-hour incubation of cells with different conjugates that had the same equivalent CPT concentration (3 nM). The results indicated that conjugation of CPT to PEG increased the proapoptotic activity of CPT. Further enhancement was achieved by using the LHRH peptide in the CPT-PEG-LHRH conjugate, the BH3 peptide in the CPT-PEG-BH3 conjugate, or a combination of these two conjugates (FIG. 3).

These results indicate that a complex drug delivery composition containing a multifunctional carrier, a cell-surface targeting moiety, an anticancer agent, and a suppressor of antiapoptotic cellular defense provides an improved means of treating cancer.

High molecular weight water-soluble polymers have been shown to preferentially accumulate in solid tumors due to the enhanced permeability and retention (EPR) effect (Minko, et al. (2000) supra; Matsumura and Maeda (1986) *Cancer Res.* 46:6387-6392; Maeda, et al. (1992) *Bioconjug. Chem.* 3:351-362; Noguchi, et al. (1998) *Jpn. J. Cancer Res.* 89:307-314). The EPR effect is the result of increased permeability of the tumor vascular endothelium to circulating macromolecules combined with limited lymphatic drainage from the tumor interstitium. It has been shown that the EPR effect leads to a significant enhancement of antitumor activity of copolymer-bound drugs and a decrease in the systemic toxicity of released drug (Minko, et al. (2000) supra; Minko, et al. (2000) supra; Kopecek, et al. (2000) supra). Healthy tissues and human ovarian carcinoma cells treated with free low molecular weight DOX or high molecular weight HPMA copolymer-bound DOX (P-DOX) reveal a significant amount of free DOX accumulation in healthy tissues. In contrast, high molecular weight P-DOX preferentially accumulates in the tumor tissues (Minko, et al. (2000) supra). Therefore, in one embodiment of the present invention, the multifunctional carrier and cell-surface targeting moiety of the complex drug delivery composition are the same molecule, a high molecular weight, water-soluble polymer.

Figure 4:
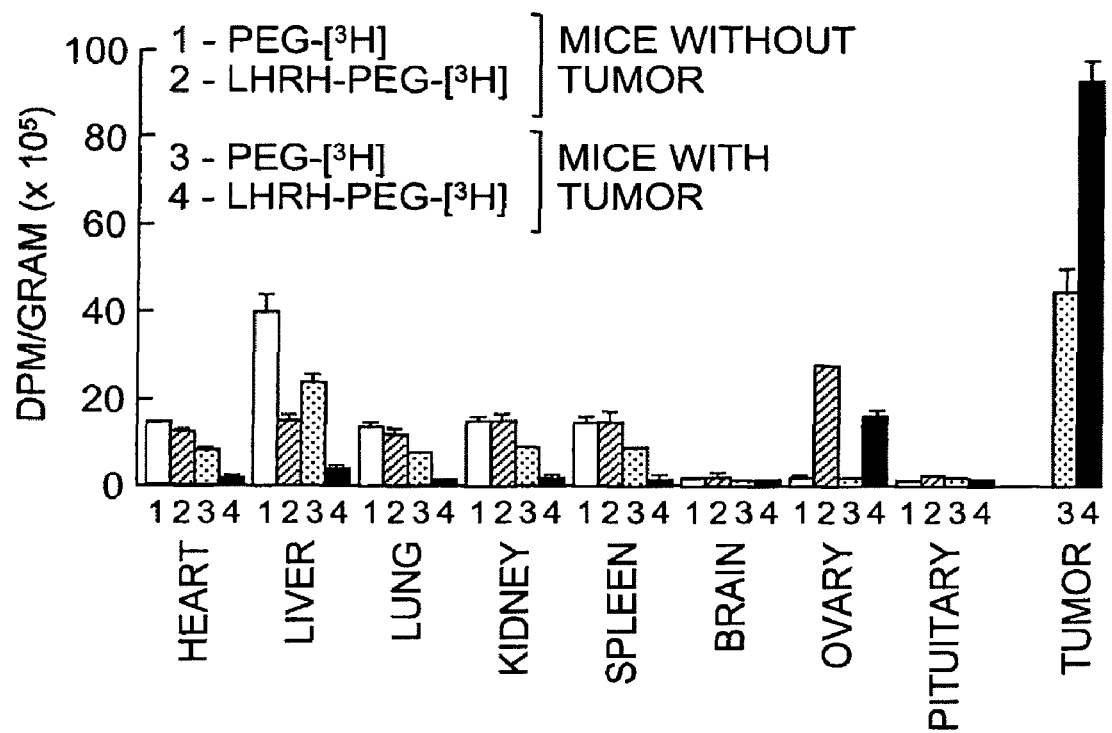
FIG. 4 shows the distribution of tritium-labeled PEG and LHRH-PEG conjugates in control mice and mice bearing human A2780 ovarian carcinoma tumors. Radioactivity is expressed in DPM per gram of tissue weight. Means ±SD are shown.

The utility of using an LHRH peptide and a high molecular weight, water-soluble polymer to target a complex drug delivery composition of the invention to tumors that express LHRH receptors was analyzed in vivo. As the sequences of the human and mouse LHRH peptide are identical, PEG and an LHRH-PEG conjugate were radiolabeled with tritium and organ distribution of the radiolabeled compositions was analyzed in nude nu/nu mice. For this analysis, six mice were used as a control and six mice received xenografts of human ovarian cancer using well-established methods (Minko, et al. (2000) *Int. J. Cancer* 86:108-117; Minko, et al. (2000) *Pharm. Res.* 17:505-514; Kopecek, et al. (2000) *Eur. J. Pharm. Biopharm.* 50:61-81). A2780 human ovarian cancer cells were subcutaneously transplanted into the flanks of female athymic nu/nu mice. When tumors reached a size of about 1 cm³ (15-18 days after inoculation), mice were treated intraperitoneally with maximum tolerated doses (10 mg/kg for the single injection) of the desired compositions. Mice without tumors received the same dose of composition. The results showed that in the absence of a tumor, non-targeted PEG polymer accumulated predominantly in the liver and at a lower level in other organs (heart, lung, kidney, spleen) (FIG. 4). Only a trace amount of non-targeted PEG polymer was found in the brain and pituitary gland indicating that PEG polymer does not breach the blood-brain and pituitary barriers. The distribution of targeted LHRH-PEG conjugate in control mice was slightly different from the non-targeted PEG polymer for most of the tissues and there was an appreciable shift from the liver to the ovary with the liver showing a reduced accumulation and the ovary showing an elevated accumulation due to the endogenous LHRH receptor present in ovaries. Tissues of mice bearing the xenografts of human ovarian tumor had observable differences in the accumulation of the compositions. Both PEG and the LHRH-PEG conjugate had a low level of accumulation in normal tissues except for the liver and ovary, wherein PEG alone accumulated in the liver and the LHRH-PEG conjugate accumulated in the ovary. Further, PEG and LHRH-PEG accumulated preferentially in ovarian tumors and LHRH-PEG did not breach the blood-brain and pituitary barriers from the systemic circulation. The lowest levels recorded were in the brain and pituitary in spite of the available LHRH receptors in the latter. The most significant accumulation was of LHRH-PEG conjugate was to the tumor. The level of accumulation was nearly twice that of PEG alone in the tumor and at least 4 times higher that other tissues. Thus, a targeted complex drug delivery composition such as LHRH-PEG can readily reach, bind and accumulate in the tumor cells that overexpress LHRH receptor.

Figure 5:
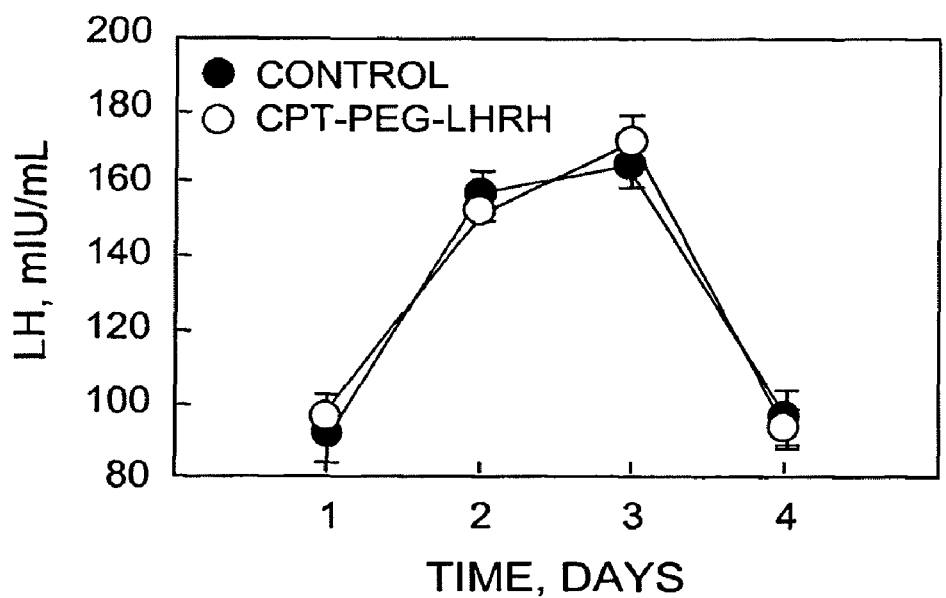
FIG. 5 shows the serum concentration of leutinizing hormone in mice treated four times with the maximum tolerated dose of CPT-PEG-LHRH conjugate and control mice treated with saline. Means ±SD are shown.

Though only trace amounts of the LHRH-PEG conjugate accumulated in the pituitary gland and brain, pituitary and brain toxicity was assessed by measuring serum levels of the leutinizing hormone (LH) and reproductive capacity in female mice treated four times within two weeks (i.e., every other day) with a maximum tolerated dose of CPT-PEG-LHRH conjugate. The maximum tolerated dose of this conjugate was equal to 2.5 mg/kg for a four-time treatment regime. Serum LH concentration was measured four times (once per day) during the average mouse estrus cycle (4 days) using an LH ELISA assay. It was found that CPT-PEG-LHRH conjugate treatment did not significantly change the profile of LH release (FIG. 5). In another series of the experiments, four female C57BL/6J wild-type mice were treated four times with a maximum tolerated dose of CPT-PEG-LHRH conjugate. After the treatment, treated or control mice were placed in one cage with a male mouse. After 3-4 weeks all mice gave birth to healthy viable offspring. The number of offspring per mouse (4-8), viability, weight change and behavior during the following four weeks were indistinguishable from the offspring of the control mice. Taken together these data indicate that when using LHRH as a cell-surface targeting moiety, a complex drug delivery compositions is not toxic to the pituitary gland.

A further embodiment of the present invention is a complex drug delivery composition wherein the multifunctional carrier, cell-surface targeting moiety, anticancer agent, and suppressor of antiapoptotic cellular defense are operably-linked to form a single molecular entity or conjugate. A complex drug delivery composition with all components operably-linked, herein referred to as a complex conjugate, exhibits a cytotoxicity and an ability to induce apoptosis to a greater extent than conjugates with two or three components operably-linked because the anticancer agent and suppressor of antiapoptotic defense are concurrently taken up by the cell. It has been shown that mixing of an anticancer agent with a suppressor of antiapoptotic defense conjugated with a cell-surface targeting moiety leads to an additive affect of cytotoxicity (Minko, et al. (2001) supra). In contrast, the effect of a complex conjugate is several orders of magnitude greater (see the logarithmic scale in FIG. 1). Further, a complex conjugate has discrete chemical components that are put together in precise combinations and molar ratios. Moreover, a complex conjugate exhibits a higher degree of specificity for the targeted tumor, due to the cell-surface targeting moiety, with reduced toxicity to healthy tissues. This specificity reduces adverse side effects on healthy tissues. Receptor-mediated endocytosis is also a more rapid process then simple endocytosis, the normal influx pathway of macromolecules into cells. In addition, the high molecular weight of the complex conjugate compared with free anticancer agent, itself provides passive targeting to solid tumors due to the EPR effect. An increase in the molecular weight of the complex conjugate amplifies the EPR effect and enhances accumulation in the tumor thereby decreasing adverse side effects. Conversely, a high molecular weight complex conjugate decreases the ability to penetrate healthy cells and significantly limits cytotoxicity. For example, the complex conjugate decreases penetration to the brain to prevent adenohypophysis cytotoxicity. It has been shown that an optimal size of water-soluble, polymer-bound, anticancer agent for effective targeting and reasonable toxicity is in the range of five to 20 kDa (Kopecek, et al. (2001) supra; DiPaola, et al. (2001) Hematol. Oncol. Clin. North Am. 15:509-524; Michaelis, et al. (2002) Anticancer Drugs 13:149-154; Kopecek, et al. (2000) Eur. J. Pharm. Biopharm. 50:61-81). It is contemplated that the molecular weight of the multifunctional carrier can be modulated to provide a complex conjugate of optimal size to enhance targeting.

By operably-linked it is meant that the individual components are combined or joined into one molecular entity or conjugate using a scaffold. In one embodiment, the complex drug delivery composition contains at least one molecule of a component combined with the scaffold. In other words, components such as the anticancer agent or cell-surface targeting moiety can have more than one molecule per complex conjugate.

Figure 6:
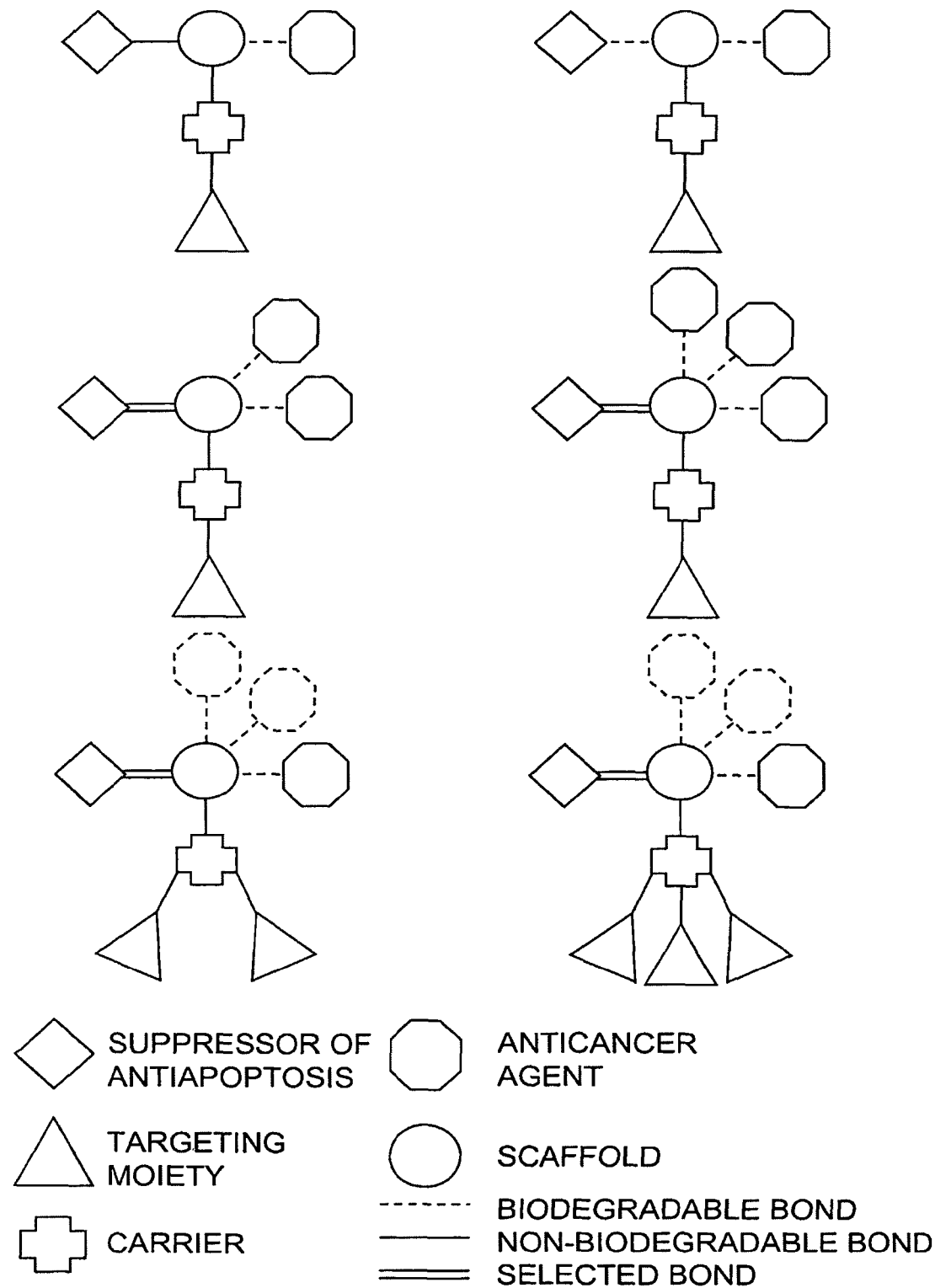
FIG. 6 illustrates exemplary species of complex conjugates of the complex drug delivery system composition of the invention.

Components of the complex conjugate can be joined or linked by non-biodegradable or biodegradable bonds (FIG. 6). A non-biodegradable bond is defined as a bond which is relatively stable in both biological fluids, such as blood or plasma, and the intracellular environment. A biodegradable bond is defined as a bond which is relatively stable in biological fluids but is easily broken inside cancer cells to release the component from the complex conjugate. In the case where one component may have a detrimental effect on another component at a certain time or place a biodegradable bond can be employed. For example, endocytosis of LHRH may result in lysosomal entrapment of the anticancer agent and/or the suppressor of antiapoptotic cellular defense. Thus, one or more linkages can be broken after binding of the cell-surface targeting moiety to its cognate receptor so that the other components will function optimally. An exemplary biodegradable linkage is a disulfide bond; nearly all the cysteine residues in circulating (blood) proteins are in the oxidized (disulfide) form whereas virtually all cysteine residues in intracellular proteins are reduced. Therefore, a disulfide bond between any two components will remain appreciably intact while in transit, and subsequently cleaved to release the two components upon exposure to the intracellular environment. See, for example, U.S. Pat. No. 6,258,774 and Huang, et al. ((1998) Bioconjugate Chem. 9:612-617) for details on disulfide biodegradable bonds.

An ester bond can also be used to achieve the desired stability of the complex drug delivery system composition in the blood stream and the desired release inside cancer cells. A further biodegradable bond which can be employed in the complex conjugate of the present invention is the Schiff base made by reacting a primary amino group with an aldehyde or ketone (Bourel-Bonnet, et al. (2003) Bioconjugate Chemistry 14:494-499). Conversely, non-biodegradable bonds include all other bonds for joining two compounds together that are not degradable, for example, single, double and triple carbon-carbon bonds; amide bonds; secondary amine linkages; thioether bonds; ether bonds; and thiocarbamate bonds. It will be appreciated by the skilled artisan that the type of bond used will vary with selected multifunctional carrier, cell-surface targeting moiety, anticancer agent, and suppressor of antiapoptotic cellular defense. For example, CPT is an inactive prodrug in a conjugated form and becomes an active drug after release from its multifunctional carrier, including removal of the peptide linker. In particular embodiments, the bond selected will improve the survivability of complex conjugate in the bloodstream as well as allow for the highest amount of active drug to be released into the tumor cell. See Conover, et al. (1997) for peptide linkages in PEG-CPT conjugates.

Wherein nucleic acid sequences, such as antisense oligonucleotides are incorporated into the complex conjugate, said nucleic acid sequences can be attached via spacer or linker molecules such as hydroxy-carboxylic acid using standard methologies.

Accordingly, another aspect of the invention is a method for producing a complex drug delivery composition. The method involves providing a scaffold and combining, joining or attaching the components of the complex conjugate to the scaffold by biodegradable or non-biodegradable bonds. Synthesis of complex conjugates can, in one embodiment, be conducted by producing each component as an independent module with subsequent attachment to the scaffold. In general, the scaffold is a peptide of 2, 3, 4, 5, 6, 7, 8, 9, or 10 amino acid residues such as poly-lysine, poly-cysteine or a combination thereof. In this manner, the stoichiometric amount and linkage to the scaffold of each component can be varied (see FIG. 6). Examples of cysteine scaffolds are provided herein. When using lysine in the scaffold, the Lys side chain amino group can be used to initiate peptide chain assembly of a component of the complex conjugate.

For example, scaffolds of two cysteine residues can be appended by three different components; the side chain thiol group of the first Cys while on the resin, the N-terminal amino group of the peptide, and the thiol side chain of the other Cys residue after cleavage from the resin by acid cleavage. The amide is formed at the C-terminus during cleavage, and it protects the scaffold peptide from carboxypeptidase digestion in body fluids when used in vivo.

For combining or attaching components to the scaffold, heterobifunctional cross-linkers are used to avoid undesired dimer formation associated with homobifunctional reagents. Thus, MAL-PEG$_{3.4K}$-NHS (Shearwater Polymers, Inc.) is a long spacer used for linking a thiol group in the scaffold to an amino group of the anticancer component (or vice versa), whereas MAL-pentane-NHS (Pierce Chemical Co., Rockford Ill.) is a short version of the same. SPDP (Pierce Chemical Co.) is an adapter that converts an amino group into a thiol group, and can be used to form either reversible disulfide or nonreversible thioether bonds. Bis-2,2'-thiopyridine disulfide (Pierce Chemical Co.) is an activator that is used to form a disulfide bond (with no spacer) between the thiol group of scaffold and the thiol group of an anticancer component.

Considering the availability of several orthogonal protecting groups on Cys and on Lys and the variety of cross-linkers, it is possible to design and synthesize many novel, multicomponent complex conjugates. For example, a scaffold peptide of:

Fmoc-Lys(Fmoc)-Cys(S—S-tButyl)-Cys(Trt)-Cys(Trt)-PAL RESIN can yield complex conjugates with two copies of a suppressor of antiapoptotic cellular defense (e.g., BH3) and two copies of anticancer agent (e.g., CPT) per multifunctional carrier (LHRH) scaffold peptide:

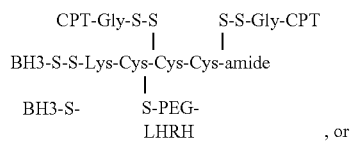

-continued

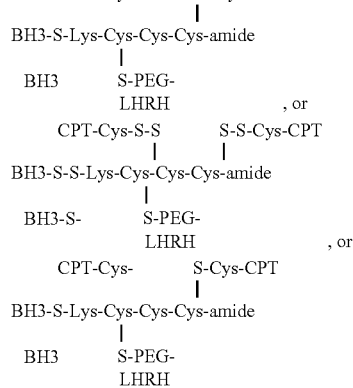

wherein, the CPT and BH3 components are attached via reducible disulfide or nonreducible thioether bonds. Furthermore, additional PEG chains can be placed between the scaffold peptide and the CPT ester and/or BH3.

Thus, as one of skill in art may appreciate, it is possible to synthesize any desired combination of components using bonds having different stability profiles in vivo and using one or more PEG spacers, if desired.

It is contemplated that the complex drug delivery composition of the present invention can be formulated into a pharmaceutical composition comprising an effective amount of the complex drug delivery composition and a pharmaceutically acceptable carrier. An effective amount of the complex drug delivery composition can be administered to the patient in a manner which ultimately decreases the signs or symptoms associated with the targeted cancer. Examples of signs and/or symptoms that can be monitored to determine the effectiveness of the composition of the invention include, but are not limited to, tumor size, feelings of weakness, weight, and pain perception. The amount of complex drug delivery composition and the specific pharmaceutically acceptable carrier will vary depending upon, for example, the anticancer component of the composition, the patient and the condition of this patient, the mode of administration, and the type of cancer being treated.

Pharmaceutically acceptable carriers are materials useful for the purpose of administering the medicament, which are preferably sterile and non-toxic, and can be solid, liquid, or gaseous materials, which are otherwise inert and medically acceptable, and are compatible with the active ingredients.

The pharmaceutical compositions can contain other active ingredients such as preservatives. The pharmaceutical compositions can take the form of a solution, emulsion, suspension, ointment, cream, granule, powder, drops, spray, tablet, capsule, sachet, lozenge, ampoule, pessary, or suppository. They can be administered by continuous or intermittent infusion, parenterally, intramuscularly, subcutaneously, intravenously, intra-arterially, intrathecally, intraarticularly, transdermally, orally, bucally, as a suppository or pessary, topically, as an aerosol, spray, or drops, depending upon whether the preparation is used to treat internal or external cancers. Such administration can be accompanied by pharmacologic studies to determine the optimal dose and schedule and would be within the skill of the ordinary practitioners.

For intravenous injection of the complex drug delivery composition, the solution can contain antioxidants, buffers, and the like. For oral administration, the complex drug delivery composition can be administered, for example, as an enterically coated preparation or as a suspension or solution. As one of skill in the art may appreciate, oral doses can be administered three or four times a day.

The complex drug delivery composition formulated for injection, can be presented in unit dose form in ampules or in multi-dose containers with an added preservative. The pharmaceutical composition can take such forms as suspensions, solutions, or emulsions in oily or aqueous vehicles, and can contain formulatory agents such as suspending, stabilizing and/or dispensing agents.

Alternatively, for cancers of the skin, or other external tissues, the complex drug delivery composition is applied to the affected part of the body of the patient as a topical ointment or cream. The composition can be presented in an ointment, for instance with a water soluble ointment base, or in a cream, for instance with an oil in water cream base.

The compounds can also be applied into body orifices such as the nose and oral cavity in the form of spray or drops. They can be applied into body orifices such as the rectum and vagina in the form of a suppository or cream.

It will be appreciated that extensive skin cancers can require the use of higher doses.

The invention is described in greater detail by the following non-limiting examples.

EXAMPLE 1

Synthesis of CPT-PEG

CPT-PEG conjugates were synthesized according to Scheme 1.

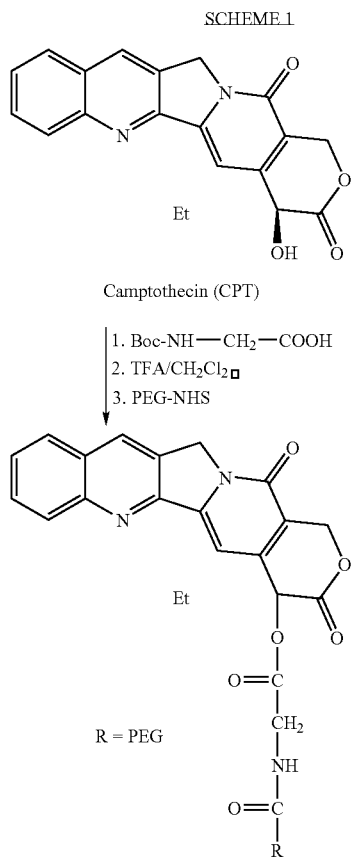

Camptothecin (CPT)

1. Boc-NH—CH$_2$—COOH
2. TFA/CH$_2$Cl$_2$
3. PEG-NHS

R = PEG

All chemicals, unless otherwise indicated, were purchased from Sigma Chemical Co. (St. Louis, Mo.) or Fisher Scientific (Houston, Tex.) and used as received. t-boc-glycine (0.31 g, 1.71 mmol; Bachem, Bioscience Inc., King of Prussia, Pa.) was dissolved in 20 mL of anhydrous methylene chloride at room temperature. To this solution was added 1,3-diisopropylcarbodiimide (DIPC, 267.7 mL, 1.71 mmol), 4-dimethylamino-pyridine (DMAP, 0.14 g, 1.14 mmol) and camptothecin (CPT, 0.20149 g, 0.57 mmol) at 0° C. While CPT (Sigma Chemical Co., St. Louis, Mo.) was dissolved in dimethyl sulfoxide (DMSO) because of its low solubility, the concentration of DMSO in working solutions was less than 1.0%; a concentration which did not have a significant effect on cells. The reaction mixture was allowed to warm to room temperature and incubated overnight. The product was washed with 0.1 N HCl, dried and evaporated under reduced pressure to yield the sold product. The product was recrystallized from methanol to give CPT-glycinate. The t-boc protection group was removed by dissolving the CPT-glycinate in a mixture of methylene chloride and trifluoracetic acid (TFA) (50:50) and stirring at room temperature for 3 hours. Solvent was evaporated under reduced pressure and precipitated using ether to give CPT-glycinate-TFA salt. CPT-glycinate-TFA salt (34.0 mg or 50 mg) and PEG-NHS (100 mg; MW ~3400; Shearwater Corporation, Huntsville, Ala.) were added to methylene chloride (5 ml) and DIEA (50 ml) was added to adjust the pH to basic. The reaction was stirred for 3 hours at room temperature. The product was recrystallized from cold ether and dried under vacuum overnight.

Conjugate structures were confirmed using several methods. MALDI-TOF mass spectrometry (PE Biosystems Voyager System 6080) of the conjugates revealed a peak at the expected molecular weight. In addition, reverse phase HPLC analysis of the unconjugated CPT and CPT-PEG exhibited different retention times; approximately 7 minutes for unconjugated CPT and approximately 5.5 minutes for the CPT-PEG conjugate. Moreover, HPLC analysis using a size exclusion column revealed a peak at approximately 11 minutes for CPT-PEG with no elution observed for the unconjugated CPT even after 1 hour. Further, dramatic increases in water solubility of the CPT-PEG conjugate over the unconjugated CPT was observed. CPT-PEG conjugate was routinely dissolved in phosphate-buffered saline, pH 7.4, and diluted with media before use (Minko, et al. (2002) supra).

EXAMPLE 2

Synthesis of CPT-amino Acid Esters

CPT-amino acid esters were synthesized according to Scheme 2.

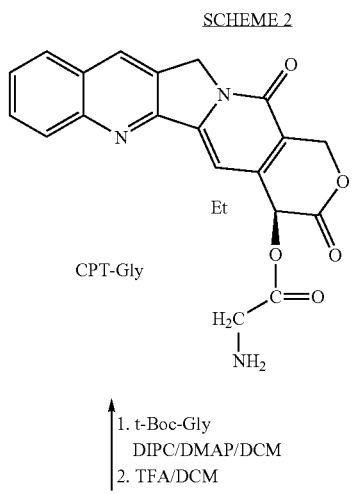

CPT-Gly 1. t-Boc-Gly
   DIPC/DMAP/DCM
2. TFA/DCM

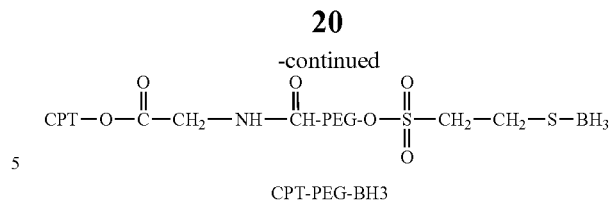

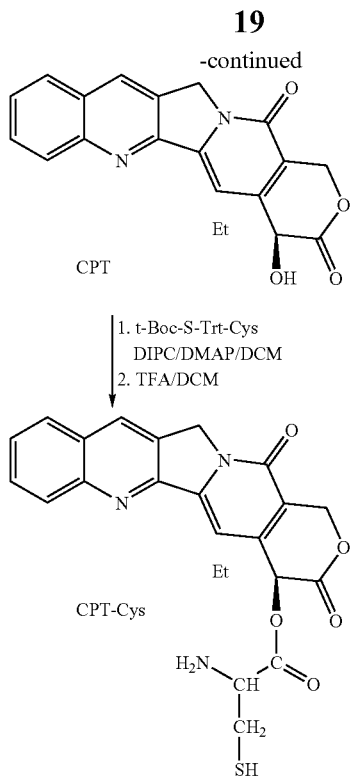

CPT was coupled to an amino acid via a biodegradable ester bond to the hydroxyl group at position 20 using a well-known method (Greenwald (2001) *J. Controlled Rel.* 74:159-171; Conover, et al. (1997) *Anticancer Res.* 17:3361-3368). A CPT-glycine ester and its conjugate to PEG via the amino group of glycine has been described (Minko, et al. (2002) supra). The CPT-cysteine conjugate was prepared by dissolving approximately 0.3 g of Boc-Cys(Trt) in 20 ml of methylene chloride. Subsequently, 1 equivalent of DIPC, 0.7 equivalents of DMAP and 0.3 equivalents of CPT were added to the Boc-Cys(Trt) and incubated overnight at room temperature. The protecting groups were removed by incubating for 1 hour in 50% TFA in methylene chloride. The CPT-cystein ester product had two potential, orthogonal conjugation sites, the amino group and the thiol group.

EXAMPLE 3

Synthesis of CPT-PEG-BH3

CPT-amino acid esters were synthesized according to Scheme 3.

SCHEME 3

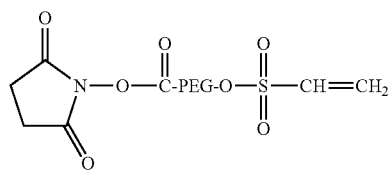

NHS-PEG-VS

1. CPT-GLY/DMF☐
2. BH3

CPT-Glycine ester was reacted with one equivalent of the bifunctional reagent, NHS-PEG-VS, in dimethylformamide (DMF), whereupon the amino group formed an amide bond with the active ester (N-hydroxysuccinimide ester of PEG). Concurrently, an analog of BH3, containing an extra residue of cysteine at the C-terminus (Ac-Met-Gly-Gln-Val-Gly-Arg-Gln-Leu-Ala-Ile-Ile-Gly-Asp-Asp-Ile-Asn-Arg-Arg-Tyr-Cys-NH$_2$: SEQ ID NO:4), was prepared by solid phase peptide synthesis. The CPT and PEG reaction mixture was combined with the BH3 analog and the thiol group of the BH3 formed a thioether bond with the VS (vinylsulfone) group on PEG. The product was recovered by ether precipitation and purified by size exclusion chromatography and ultrafiltration to remove any CPT esters or BH3. Size exclusion chromatography was conducted using a mobile phase containing 30% acetonitrile, 70% water buffered with 50 mM triethylamine/acetic acid, pH 6.0. The collected peak was dried and weighed.

EXAMPLE 4

Synthesis of CPT-PEG-LHRH

CPT-amino acid esters were synthesized according to Scheme 4.

SCHEME 4

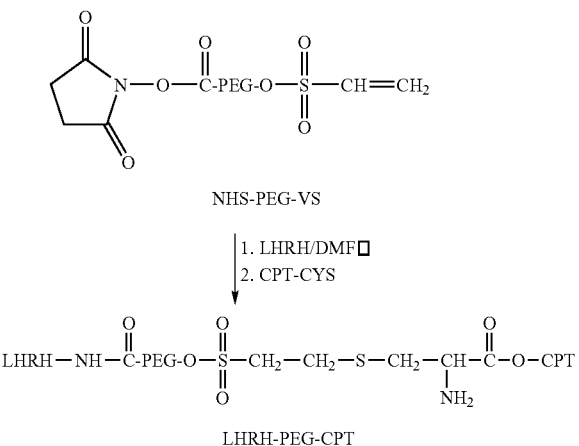

A LHRH analog, LHRH-Lys[6]-des-Gly[10]-Pro[9]-ethylamide (SEQ ID NO:3), having a reactive amino group only on the side chain of Lys-6, was reacted with one equivalent of NHS-PEG-VS, in DMF. CPT-Cysteine was subsequently added to achieve thioether bond formation between the VS group and the thiol group. The product was recovered by ether precipitation and purified by size as exclusion chromatography and ultrafiltration as describe herein.

EXAMPLE 5

Complex Conjugates

Biodegradable linkage between CPT and the multifunctional carrier and non-biodegradable linkages between BH3 and LHRH peptides and the multifunctional carrier. CPT is linked to the scaffold peptide using a glycine ester bond. CPT is prepared in a prodrug form as an ester of glycine:

CPT-OH+COOH—CH$_2$—NH$_2$->CPT-O—C(=O)—CH$_2$—NH$_2$

The CPT-glycine ester has one amino group for linkage to the scaffold. The activated CPT ester is produced:

CPT-Gly ester+NHS—(CH$_2$)$_5$-MAL->CPT-Gly-MAL and attached to a thiol group on the scaffold peptide. The ester bond has been shown to be relatively stable in the blood stream, providing an inactive form of CPT until it was easily degraded in the tumor environment (Greenwald (2001) supra; Conover, et al. (1997) supra). The BH3 peptide is linked to the scaffold peptide by a non-degradable thioether bond, while the LHRH is linked to the PEG polymer via an amide non-degradable bond. Like the CPT-PEG-LHRH conjugates, the complex conjugates contain the more potent agonist LHRH-Lys[6], having only one amino group for coupling to the scaffold. The amino group of this analog can be derivatized without loss of affinity for the LHRH receptor (Conn and Hazum (1981) *Endocrinology* 109:2040-2045). In addition, this peptide does not have thiol groups that may otherwise interfere with the scaffold peptide. The LHRH is linked directly to PEG. PEG minimizes steric hindrance by acting as a spacer molecule between the LHRH and the scaffold peptide. As a linker to connect LHRH to the scaffold, a bifunctional PEG is used (Shearwater Polymers Inc., Huntsville, Ala.). The various bonds between LHRH, PEG and the scaffold are considered to be relatively stable in vivo. The LHRH analog itself is considered to be relatively peptidase resistant (Conn and Hazum (1981) supra). LHRH is reacted in solution phase with the PEG cross-linker, whereby an amide bond is formed between the amino group and the NHS group:

LHRH-Lys[6]-NHEt+NHS-PEG-MAL->LHRH-PEG-MAL (The reactive groups, the lysine side chain and NHS on PEG, are both shown on the left side of the equation, but their product, an amide bond, is not shown on the right side.) By using an excess of LHRH (e.g., 1.5 equivalents) there is no leftover MAL-PEG-NHS which may yield undesired side products.

Biodegradable linkage between CPT and BH3 peptide and a scaffold peptide and non-biodegradable linkage between LHRH peptide and a PEG carrier. CPT was linked to the scaffold peptide by the biodegradable glycine-ester bond as described, the BH3 peptide was linked to the scaffold peptide by a biodegradable disulfide bond, while the LHRH peptide was linked to the PEG polymer via an amide non-degradable bond as described. When CPT is linked to the complex conjugate, a biodegradable bond is desirable. Cleavage of this bond inside cancer cells converts a non-active prodrug into active drug that possesses a high anticancer activity.

Two and three molecules of the anticancer agent (CPT) attached to the complex conjugate. Two or three molecules of CPT are linked to a scaffold peptide via biodegradable glycine ester bonds. The LHRH peptide is linked to the PEG polymer via amide non-degradable bond as described. BH3 peptide can be appended to the scaffold by either a biodegradable or non-biodegradable linker. Native BH3 peptide has only one primary amino group at the N-terminus which can be used to form a stable linkage to the scaffold. However, the BH3 analog provide herein, having an extra C-terminal cysteine residue, can be coupled via its thiol group using a reversible disulfide bond or a nonreversible thioether bond.

An increase in the number of CPT molecules per conjugate may lead to a decrease in the solubility of complex conjugate. Three molecules of CPT per conjugate may represent the upper limit for this parameter. If an optimal ratio is not obtained with three molecules of CPT per complex conjugate, a more soluble derivative of CPT (e.g., Topotecan) is considered.

Two and three molecules of the cell-surface targeting moiety (LHRH) attached to the complex conjugate. Anticancer activity and targeting of complex conjugate can be modulated by the number of copies of the cell-surface targeting moiety. Two or three molecules of the LHRH peptide will be attached to the complex conjugate via an amide non-degradable bond. As demonstrated herein, very low concentrations of LHRH are required to saturate the LHRH receptor and high cytotoxicity is produced by a CPT-PEG-LHRH conjugate containing only one copy of LHRH. Thus, suitable targeting of complex to cancer cells can be achieved with one or two molecules of LHRH per complex conjugate.

It is desirable to increase the number of molecules of anticancer agent per one complex conjugate to the highest possible level in order to increase the cytotoxicity and decrease the cost of complex conjugate. Further, it is desirable to provide effective targeting of an anticancer agent specifically to cancer cells to minimize adverse side effects.

Attachment of components to Scaffold. The complex conjugate was synthesized by solid phase synthesis on PAL resin using Fmoc chemistry. PAL resin was derivatized with Fmoc-Cys(Trt) using one of several standard coupling reagents such as HOBt (hydroxybenzotriazole) and BOP (benzotriazol-1-yloxy-tris(dimethylamino)phosphonium hexafluorophosphate). Solid phase synthesis on PAL resin gives:

Fmoc-Cys(S—S-tButyl)-Cys(Trt)-PAL RESIN

A disulfide bond is indicated by "S—S" while a thioether bond is indicated by "—S—". The disulfide-linked mercapto-tButyl group was selectively removed from the Cys side-chain thiol group by treatment with a reducing agent (e.g., dithiothreitol) under slightly basic pH to expose the first conjugation site:

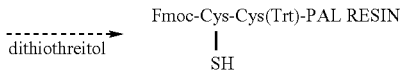

The conjugate was then built stepwise on the solid support, which was washed free of reagents and byproducts after each step.

The activated LHRH-PEG component described herein was reacted with the scaffold peptide on the resin:

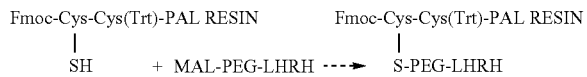

The Fmoc group was removed from the N-terminal amino group by treatment with 20% piperidine in DMF to expose the second conjugation site.

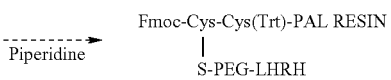

The deprotected amino group of the conjugate was reacted with the disulfide reagent, converting it functionally into an activated thiol (i.e., the thiopyridine adduct).

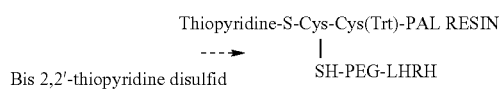
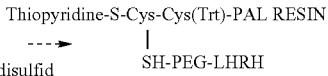

Thiopyridine-S-Cys-Cys(Trt)-PAL RESIN
|
Bis 2,2'-thiopyridine disulfid    SH-PEG-LHRH After washing the resin with DMF, BH3-SH was added in stoichiometric amounts.

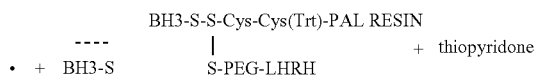

BH3-S-S-Cys-Cys(Trt)-PAL RESIN
· + BH3-S            |                + thiopyridone
            S-PEG-LHRH Completeness of reaction was determined by the plateau in absorbance at 340 nm from the displaced thiopyridone group when additional BH3-SH was added.

Alternatively, SPDP can be used instead of the thiopyridine reagent on the piperidine-treated resin to give the nonreducible product. SPDP converts the scaffold amino group into a maleimide group, which causes the formation of a thioether bond with BH3-SH, as follows:

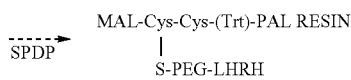

MAL-Cys-Cys-(Trt)-PAL RESIN
SPDP              |
            S-PEG-LHRH

After washing the resin with DMF, BH3-SH is added to form the non-reducible thioether:

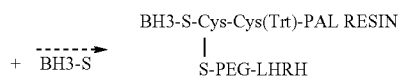

BH3-S-Cys-Cys(Trt)-PAL RESIN
+ BH3-S           |
            S-PEG-LHRH

Cleavage of the two versions from the resin in strong acid produces an intermediate, the 2-component conjugate in which the suppressor of antiapoptosis, BH3, is held by (1) a reducible disulfide or (2) nonreducible thioether bond; in both cases the targeting group, LHRH, is held by a nonreducible thioether bond, as follows:

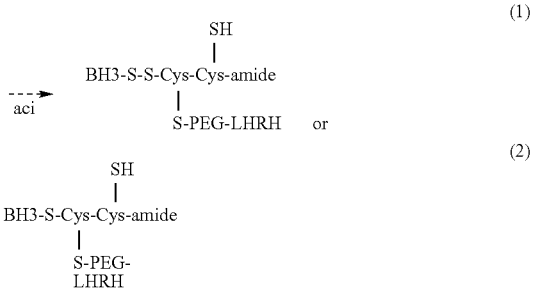

SH                              (1)
        |
BH3-S-S-Cys-Cys-amide
aci       |
        S-PEG-LHRH     or
                                        (2)
        SH
        |
BH3-S-Cys-Cys-amide
        |
        S-PEG-
        LHRH The trityl group is simultaneously removed by the acid treatment to expose the third conjugation site, which can be reacted with MAL-Gly-CPT to form:

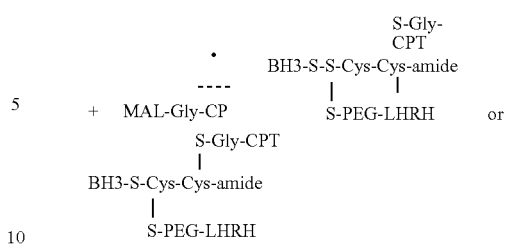

S-Gly-CPT
                        |
            BH3-S-S-Cys-Cys-amide
+ MAL-Gly-CP        |           S-PEG-LHRH    or
            S-Gly-CPT
            |
BH3-S-Cys-Cys-amide
            |
        S-PEG-LHRH Alternatively, the newly exposed thiol group on the scaffold can be activated in a reaction with bis-2,2' thiopyridine disulfide.

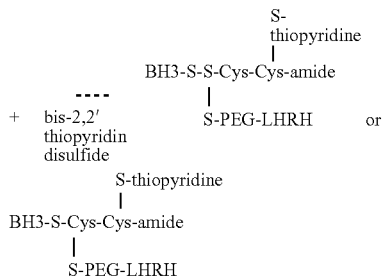

S-thiopyridine
                    |
        BH3-S-S-Cys-Cys-amide
+ bis-2,2'        |          S-PEG-LHRH    or
  thiopyridin
  disulfide
        S-thiopyridine
        |
BH3-S-Cys-Cys-amide
        |
    S-PEG-LHRH This conjugate is reacted with a CPT-Cys ester to yield a disulfide linkage:

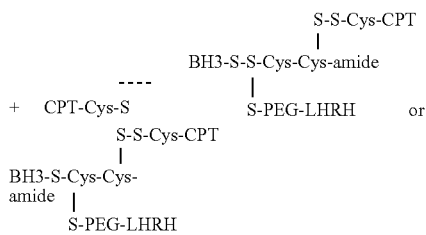

S-S-Cys-CPT
                        |
            BH3-S-S-Cys-Cys-amide
+ CPT-Cys-S       |          S-PEG-LHRH    or
            S-S-Cys-CPT
            |
BH3-S-Cys-Cys-
amide   |
    S-PEG-LHRH Three other versions are also formed in addition to those indicated above.

Four complex conjugates having reducible disulfide or nonreducible thioether bonds associated with BH3 and CPT are provided which contain all four components of the complex drug delivery composition of the invention. The conjugates with the CPT added as a Cys ester have two unstable bonds (ester and disulfide) holding the anticancer drug, camptothecin, to the other three components of the conjugate.

Ether precipitation (10 volumes), dialysis (10,000 cut-off), ultrafiltration or size exclusion chromatography are used to concentrate and purify the product. Mass spectrometry and amino acid analysis are used for quality control.

EXAMPLE 6

Cellular Uptake and Retention

The in vitro release of appended components with biodegradable bonds (e.g., CPT, BH3) or stability of non-releasable components (e.g., LHRH, BH3) are investigated in experimental buffers and biological matrices (plasma, cancer cells, tissue homogenates of the intestine, liver, brain). The release of the components by biodegradable bonds is analyzed by using a sample of conjugate solution prepared in biological matrix (e.g., the experimental buffer). The sample is incubated for 2 hours at 37° C. A control study without conjugate is run in parallel. Samples are withdrawn over time with initial concentrations of drug equal to 0.1 µM and 25 µM. A sample of the solution is then placed on a MICROCON™ filter (molecular weight cut-off=3000 Da) (Amicon Inc., Beverly, Mass.) and centrifuged at 12,000×g for 30 minutes. The unstable conjugate passes through the filter whereas the intact conjugate is retained. Free or conjugated drug are measured and release rates calculated.

The stability/release in plasma is also measured. Plasma is obtained from a commercial source. Fifty µl of various concentrations of the complex conjugate are spiked into a tube containing prewarmed plasma. All studies are performed in triplicate. Tubes are placed in a 37° C. shaking water bath (100 rpm) for 2 hours. Samples are removed at 0, 30, 60, 90, and 120 minutes. Removed samples are mixed immediately with 50 mM phosphate-buffer saline (PBS, pH 7.4) and 500 µl of methanol (1:20 final dilution) at 4° C. to quench the reaction. Samples are centrifuged at 3000×g for 30 minutes at 4° C. and the supernatant is transferred to a 96-well plate for HPLC injection.

The stability/release in other biological matrices is also determined. Cells or homogenates (from tissues, cells) are incubated with each radiolabeled conjugate. Total uptake is measured with time. At time zero, and periodically thereafter, aliquots of culture medium and cellular extract are ultrafiltered to determine the amount of release of free drug from the conjugate. In separate experiments, the conjugate is incubated under argon with culture medium or with cell-free extract; aliquots taken at time points are ultrafiltered and counted. In another experiment, cells are incubated for different time periods with radiolabeled conjugate and homogenized under conditions that give maximum lysis, as observed by microscopy and minimal lysis of lysosomes and as determined by assay of the marker enzyme, beta-galactosidase.

The uptake/accumulation/retention studies are carried out using well-known methods (Minko, et al. (1999) *Pharm. Res.* 16:986-996; Guo, et al. (1999) *J. Pharmacol. Exp. Ther.* 289: 448-454). Briefly, cells are grown in RPMI 1640 medium supplemented with 10% fetal bovine serum, 10 µg/ml insulin, 100 U/ml penicillin and 100 µg/ml streptomycin and are maintained at 37° C. in a humidified atmosphere of 5% $CO_2$ in air. Accumulation/uptake studies are performed in 12.5 $cm^2$ tissue-culture flasks containing approximately $1 \times 10^7$ in 4 ml media with 2-5 replicates flasks for each time point. Cells are incubated with various concentrations of the conjugate for 0, 15, 30, 45, 60, 75, 90, 105, 120 and 240 minutes or longer, if required. At the end of each incubation period, drug-containing medium is removed and the monolayer cells are washed three times with ice-cold PBS. The cells are lysed with 0.1% TRITON®-X100 and mechanically harvested from flasks by repeatedly pipetting the cell lysate for a brief period. Free and conjugated drug concentrations are determined by the analytical methods provided herein.

Intracellular localization of active components of the complex conjugate (anticancer agent, suppressor of antiapoptotic cellular defense and cell-surface targeting moiety) is analyzed by fluorescent and confocal microscopy. To this end, peptides that do not demonstrate significant native fluorescence are labeled with different fluorescent labels prior to incorporation into the complex conjugate using well-known methods (Minko, et al. (2001) *J. Controlled Rel.* 71:227-237; Kopecek, et al. (2000) *Eur. J. Pharma. Biopham.* 50:61-81).

Alternatively, the multifunctional carrier is assayed. PEG conjugates are assayed using an ELISA method (Tsai, et al. (2001) *Biotechniques* 30:396-402).

EXAMPLE 7

Anticancer Effectiveness

CPT concentrations were measured by PE Sciex API-365 liquid chromatography-tandem mass spectrometers (LC/MS/MS) with APCI or ESI modes. 12-nitro-camptothecin (12-NC) was used as an internal standard. HPLC separation was achieved with a Zorbax XDB-C18 column prior to MS/MS detection.

Cell culture. Sensitive (A2780) and multidrug resistant (A2780/AD) variants of human ovarian carcinoma cell lines were analyzed. Other cell types with different expression of LHRH receptor (SKOV-3, PC-3, MCF-7) were obtained from ATCC (Manassas, Va.). Cells were cultured in RPMI 1640 medium (Sigma Chemical Co., St. Louis, Mo.) supplemented with 10% fetal bovine serum (HyClone, Logan, Utah). Cells were grown at 37° C. in a humidified atmosphere of 5% $CO_2$ (v/v) in air and were free of Mycoplasma as tested by the use of PCR Mycoplasma detection kit (ATCC, Manassas, Va.). All experiments were performed on cells in the exponential growth phase. Based on the results of in vitro studies, several cell lines were selected for an in vivo model of cancer.

Controls. Complex drug delivery compositions with scrambled BH3 and LHRH peptide sequences were used as controls.

Cytotoxicity. The cytotoxicity of drugs were assessed using a modified MTT (3-(4,5-dimethylthiazol-2-yl)-2,5-diphenyltetrazolium bromide) assay (Kunath, et al. (2000) *Eur. J. Pharm. Biopharm* 49:11-15; Minko, et al. (1998) *J. Controlled Rel.* 54:223-233; Minko, et al. (1999) *J. Controlled Rel.* 59:133-148; Minko, et al. (2002) *Cancer Chemother. Pharmacol.* 50:143-150). To measure cytotoxicity, cells were incubated in a 96-well microtiter plate with 45 different equivalent concentrations of CPT ranging from $2^{10}$ to $2^{44}$ in a complex conjugate. Six wells were used for control cells. The duration of incubation was varied from 3 to 72 hours to find an optimal range of incubation time for each complex conjugate.

Apoptosis. Two approaches were used to assess apoptosis induction. The first approach was based on measuring the enrichment of cell cytoplasm by histone-associated DNA fragments (mono- and oligo-nucleosomes) using anti-histone and anti-DNA antibodies (Cell Death ELISA Plus kit, Roche Diagnostics, Rockford, Ill.) as previously described (Minko, et al. (2002) supra; Minko, et al. (1999) supra; Minko, et al. (2000) supra). The method was used to analyze time- (0, 1, 2, 3, 4, 12, 24, 36, 48, 72 hours) and concentration- (0.1 to $10 \times IC_{50}$) dependent apoptosis induction in A2780 cells. The second approach was based on the detection of single- and double-stranded DNA breaks (nicks) by in situ cell death detection kit (Roche Diagnostics, Rockford, Ill.) using terminal deoxynucleotidyl transferase mediated dUTP-fluorescein nick end labeling (TUNEL) method (Minko, et al. (2002) supra; Minko, et al. (1999) supra). After incubation with selected concentrations of complex conjugates, cells were fixed, permeabilized and incubated with the TUNEL reaction mixture. Time incubation and concentration of active components of the complex conjugates were selected based on the results of the ELISA measurements. The label incorporated at the damaged sites of the DNA was visualized by a fluorescence microscope and quantified by a flow cytometer (Minko, et al. (1999) supra; Kopecek, et al. (2000) supra).

Cell death signaling pathways. To characterize the cell death signaling pathways, the expression of p53, c-fos, c-jun, proapoptotic (BAD, BAX, BCL-G, BCL-W, BCL-XS, BID, BIK, BIM, BNIP 1-3, HARAKIR1, MSL-1S, NIX) and anti-apoptotic (BCL-2, AVEN, BAG, BCL-XL, BFL, DAD1, MSL-1) members of BCL-2 family of proteins and genes encoding these proteins were measured by western blot analysis and RT-PCR, respectively using well-established methods known to those of skill in the art.

Cystein aspartate-specific proteases (caspases). Three approaches were used to analyze the role of each of the human caspases in the apoptosis induction. First, the expression of genes encoding human caspases 1-10 and the Apoptotic Protease Activating Factor (APAF-1) and Second Mitochondria-Derived Activator of Caspase (SMAC) were studied by RT-PCR (Minko, et al. (1999) supra; Minko, et al. (2000) supra). However, in the case of caspases, gene expression does not always reflect the actual activity of caspases; the gene encodes a so-called procaspase, an inactive form of caspase, which later may or may not be converted into the active form. Therefore, in addition to the measurement of the gene expression, the amount of active caspases and activity of the enzymes was measured. The amount of active caspases was estimated by western blot analysis. The activity of expressed caspases was measured using the Caspase Protease Assay kit (MBL International, Watertown, Mass.) or a colorimetric protease assay kit (PanVera, Madison, Wis.) (Minko, et al. (2001) supra). Cells were separately incubated with the conjugates for 48 hours. The assay colormetric assay is based on the spectrophotometric detection of the chromophore p-nitroanilide (pNA) after cleavage from the substrate, X-pNA. An increase in caspase activity was determined by comparing levels in cells exposed to conjugates to levels in cells of the untreated control incubated with saline.

DNA repair, replication and biosynthesis. The key enzymes in this process are topoisomerases and thymidine kinases that are encoded by TOP1 and TOP2 and TK1 genes, which were assessed by RT-PCR using well-known methods (Minko, et al. (1999) supra; Minko, et al. (2000) supra).

Gene expression. A combination of reverse transcription (RT) and polymerase chain reaction (PCR) was used for the analysis of gene expression as described (Minko, et al. (1999) *J. Controlled Rel.* 59:133-148). Briefly, total cellular RNA was isolated using an RNeasy kit (QIAGEN,™, Valencia, Calif.) and a QIASHREDER™ micro-spin homogenizer (QIAGEN). First-strand cDNA was synthesized by Ready-To-Go You-Prime First-Strand Beads (Amersham Biosciences, Piscataway, N.J.) according to the manufacturer's instructions with 2 µg of total cellular RNA (from $1 \times 10^7$ cells) and 100 ng of random hexadeoxynucleotide primer (Amersham Biosciences, Piscataway, N.J.). After synthesis, the reaction mixture was diluted 1:3 with water and immediately subjected to PCR, which was carried out using GenAmp PCR System 2400 (Perkin Elmer Instruments, Shelton, Conn.). The pairs of primers used to amplify each type of cDNA and PCR regimes are well-known in the art (Kunath, et al. (2000) supra; Minko, et al. (2003) supra; Minko, et al. (2002) supra; Minko, et al. (1999) supra; Minko, et al. (2000) supra; Minko, et al. (2001) supra). PCR products were separated in 4% NUSIEVE® 3:1 RELIANT® agarose gels (BMA, East Rutherford, N.J.) in 1×TBE buffer (0.089 M Tris/Borate, 0.002 M EDTA, pH 8.3) by submarine electrophoresis. The gels were stained with ethidium bromide and digitally photographed. To calculate the size and amount of PCR products, a Low DNA Mass ladder (GibcoBRL, Carlsbad, Calif.) was used. $\beta_2$-microglobulin was used as an internal standard and to confirm the efficacy of PCR (Kunath, et al. (2000) supra; Minko, et al. (2001) supra).

Protein expression. The identification and estimation of the amount of expressed proteins was performed by western immunoblotting analysis using commercial antibodies (StressGene Biotechnologies Corp., San Diego, Calif.) according to the manufacturer's recommendations (Pakunlu, et al. (2003) supra).

EXAMPLE 8

Pharmacokinetics, Tumor and Organ Accumulation and Distribution

In vivo stability/release is investigated using rabbits. Briefly, the conjugate is injected intravenously into rabbits and blood levels are determined by HPLC. Without reductive cleavage, only the released anticancer agent is present in the sample measured by HPLC. With reductive cleavage using DTT, the anticancer agent is released from the conjugate in the sample so that the sum of both forms of the anticancer agent is measured. If, at every time point, the concentration of free anticancer agent is found to be the same in both the DTT-treated and the untreated samples, this indicates that the anticancer agent was rapidly released from its PEG carrier in vivo. A reverse transcriptase inhibition assay is used to confirm that the anticancer agent released in blood is the active form. As a control, an authentic anticancer agent is run on the HPLC column. An aliquot of each HPLC fraction is analyzed for anticancer agent activity.

Pharmacokinetics, tumor and organ distribution of the conjugates and components thereof are performed. Female, nu/nu mice bearing xenografts of human cancer xenografts are fasted 12-18 hours prior to the study in individual cages with free access to water. A solution of each conjugate (0.1 ml, 0.1 mg/100 g body weight) is given by intravenous (iv) injection through the tail vein or orally by gavage. Each group consists of three mice unless otherwise indicated. The mice are euthanized by $CO_2$ asphyxiation at 0.05, 0.25, 1, 2, 4, 6, and 24 hours after dosing. Blood is directly collected into a heparinized syringe from the heart of mice that had received an iv injection of the conjugates. The non-reproductive (brain, heart, lung, liver, kidneys, spleen, and intestine) and reproductive organs (breast, ovary and uterus) are harvested and rinsed with PBS to wash away blood attached around the organs and weighed prior to freezing. Plasma and tissue samples are stored at −80° C. For analysis of tissues, samples are thawed and an extraction solution (60% acetonitrile in 0.1% trifluoroacetic acid) is added to reach a final ratio of 10 ml/g. Samples are homogenized (12,000 rpm for 1 minute) in an ice bath and centrifuged (1600×g, 10 minutes). The supernatant is transferred into a tube and vacuum-dried. 250 µl of PBS is added to dissolve the dried sample and used for analysis. The organs/tissues selected for collection were chosen as they may play an important role in the elimination of the conjugates (intestine, kidney, liver and spleen), are the target organs of interest for drug delivery (ovaries, uterus, breast, tumor), or are important for assessing the pharmacokinetics (blood).

Antitumor activity in an animal model is conducted. Nude mice models of human xenografts are used (Kopecek, et al. (2001) supra; Minko, et al. (1999) supra; Minko, et al. (2000) supra; Minko, et al. (2001) supra; Kopecek, et al. (2001) supra). Selected human cancer cells ($5 \times 10^6$) are subcutaneously transplanted into the flanks of female athymic nu/nu mice. When the tumors reach a size of about 1 cm³ (13-18 days after inoculation), mice are treated intraperitoneally for several weeks (1st and 4th days of each week) with the maximum tolerated doses of drugs. These maximum tolerated drug doses are estimated based on animal weight changes after the injection of increasing doses of drugs as previously described (Minko, et al. (2000) supra; Kopecek, et al. (2001) supra). Tumor size is measured in all animals before each injection. Tumor mass is determined after sacrificing a portion of the total number of animals. The experiments are stopped after tumor mass reaches 10% of the animal's body weight. Control animals receive an equivalent volume of saline.

The suppression of tumor growth is used as an indicator of antitumor activity of complex conjugates. Tumor size is measured twice per week in each animal. Tumor mass is measured after sacrificing the animals weekly Cell-death induction in tumor and healthy organ tissues (the brain, heart, lung, liver, kidney, spleen, ovary, breast, uterus) is measured using methods provided herein. The measurement of apoptosis induction on healthy organs is used to characterize adverse side affects of the drugs.

EXAMPLE 9

Statistical Analyses

Analysis of Transport/Uptake Data. The initial rate of drug disappearance is estimated from the initial slope of the semi-logarithmic plot of drug concentration versus incubation time. Linear regression analysis is performed on the data and the initial drug concentration is taken as the intercept of the log concentration axis. The disappearance rate constant is taken from the slope of the regression line. The degradation rate is the product of the initial rate constant and the initial concentration of drug. For first order disappearance, the half-life is calculated using $t_{1/2}=0.693/k_{diss}$.

Statistical and Numerical Analysis. The number of animals in each point (as well as a number of independent measurements in vitro) is at least 7. The difference between variants is considered significant if P<0.05, determined by single factor analysis of variance (ANOVA). Data is expressed as mean ±S.D.

Pharmacokinetic Data Analysis and Models. Plasma concentration-time data are analyzed by standard compartmental and/or non-compartmental pharmacokinetic methods (Gibaldi and Perrier, In: Pharmacokinetics, New York, Mercel Dekker, 1982, pp 271-318). The highest observed concentration and the corresponding sampling time are defined as $C_{max}$ and $t_{max}$, respectively. The elimination half-life ($t_{1/2}$) is estimated from $t_{1/2}=\ln2/l$ where l is the slope of the regression line that best fit the terminal portion of the log-linear concentration time curve. The area under the concentration time curve (AUC) is calculated by a combination of the trapezoidal and log-trapezoidal methods (Chiou (1978) *J. Pharmacokinet. Biopharm.* 6:539-546), and extrapolated to infinity.

---

What is claimed is:

1. A method of inducing tumor cell death in a patient diagnosed with a luteinizing hormone releasing hormone receptor (LHRHR)-positive tumor, comprising administering to said patient a composition comprising (i) a BH3 peptide; (ii) an anti-tumor agent; and (iii) a peptide targeting LHRHR; wherein said BH3 peptide, said anti-tumor agent and said peptide targeting LHRHR are attached to a scaffold peptide or water-soluble polymer, so that simultaneous uptake of said BH3 peptide and said anti-tumor agent by said LHRHR-positive tumor cells occurs.

2. The method of claim 1, wherein at least one of said peptide targeting LHRHR, said BH3 peptide or said anti-tumor agent are covalently attached to a scaffold peptide by means of a bifunctional water-soluble polymer.

3. The method of claim 1, wherein at least one of said peptide targeting LHRHR, said BH3 peptide or said anti-tumor agent are covalently attached to a scaffold peptide.

4. The method of claim 3, wherein said BH3 peptide, said peptide targeting LHRHR and said anti-tumor agent are covalently attached to the same scaffold peptide.

5. The method of claim 4, wherein at least one of said BH3 peptide, said peptide targeting LHRHR or said anti-tumor agent are covalently attached to a scaffold peptide by means of a bi-functional water-soluble polymer.

6. The method of claim 3, wherein two of said BH3 peptide, said peptide targeting LHRHR and said anti-tumor agent are covalently attached to opposite ends of a bi-functional water-soluble polymer.

7. The method of claim 1, wherein said anti-tumor agent is selected from the group consisting of taxol, cytochalasin B, gramicidin D, ethidium bromide, emetine, mitomycin, etoposide, tenoposide, vincristine, vinblastine, camptothecin (CPT), colchicin, doxorubicin, daunorubicin, mitoxantrone, mithramycin, actinomycin D, 1-dehydrotestosterone, glucocorti-coids, procaine, tetracaine, lidocaine, propranolol, puromycin, methotrexate, 6-mercaptopurine, 6-thioguanine, cytarabine, 5-fluorouracil, decarbazine, mechlorethamine, thiotepa, chlorambucil, melphalan, carmustine (BCNU), lomustine (CCNU), cyclophosphamide, busulfan, dibromo-mannitol, streptozotocin, mitomycin C, cis-dichlorodiamine platinum (II) (DDP), cisplatin, dactinomycin, bleomycin, mithramycin, anthramycin (AMC), exisulind, 2-methoxyestradiol, bortezomib and combinations thereof.

8. The method of claim 7, wherein said anticancer agent is camptothecin.

9. The method of claim 1, wherein said peptide targeting LHRHR is LHRH.

10. A method of inducing tumor cell death in a patient suffering from an LHRHR-positive tumor comprising
(a) identifying a patient having over-expressed LHRHR tumor cells in a tissue of interest,
(b) administering to said patient a composition comprising
  (i) a BH3 peptide;
  (ii) an anti-tumor agent; and
  (iii) a peptide targeting LHRHR,
wherein said BH3 peptide, said anti-tumor agent and said peptide targeting LHRHR are attached to a scaffold peptide or water-soluble polymer, so that simultaneous uptake of said BH3 peptide, and said anti-tumor agent by over-expressed LHRHR tumor cells occurs.

11. The method of claim 10, wherein said method anti-tumor agent is selected from the group consisting of taxol, cytochalasin B, gramicidin D, ethidium bromide, emetine, mitomy-cin, etoposide, tenoposide, vincristine, vinblastine, camptothecin (CPT), colchicin, doxorubicin, daunorubicin, mitoxantrone, mithramycin, actinomycin D, 1-dehydrotestosterone, glucocorti-coids, procaine, tetracaine, lidocaine, propranolol, puromycin, methotrexate, 6-mercaptopurine, 6-thioguanine, cytarabine, 5-fluorouracil, decarbazine, mechlorethamine, thiotepa, chlorambucil, melphalan, carmustine (BCNU), lomustine (CCNU), cyclophosphamide, busulfan, dibromo-mannitol, streptozotocin, mitomycin C, cis-dichlorodiamine platinum (II) (DDP), cisplatin, dactinomycin, bleomycin, mithramycin, anthramycin (AMC), exisulind, 2-methoxyestradiol, bortezomib and combinations thereof.

12. The method of claim 11, wherein said anti-tumor agent is selected from the group consisting of taxol, doxorubicin and camptothecin.

13. The method of claim 10, wherein said peptide targeting LHRHR is LHRH.

14. The method of claim 13, wherein said peptide targeting LHRHR is LHRH having the structure of SEQ ID No. 3.

15. The method of claim 13, wherein said water soluble polymer is selected from the group consisting of N(2-hydroxypropyl)methacrylmide HPMA copolymer, styrenemaleic-anhydride copolymer, PEG, polypropylene oxide, polyglutamic acid and dextran.

16. The method of claim 15, wherein said polymer is a PEG having molecular weight ranging from 200 to 35000.

17. The method of claim 16, wherein said PEG has a molecular weight between 200 and 3500.

* * * * *